US011878080B2

(12) United States Patent
Knowles et al.

(10) Patent No.: US 11,878,080 B2
(45) Date of Patent: Jan. 23, 2024

(54) PROTEIN CAPSULES

(71) Applicants: Cambridge Enterprise Limited, Cambridge (GB); President and Fellows of Harvard College, Cambridge, MA (US)

(72) Inventors: Tuomas Knowles, Cambridge (GB); Ulyana Shimanovich, Cambridge (GB); Christopher Dobson, Cambridge (GB); David Weitz, Cambridge, MA (US)

(73) Assignees: CAMBRIDGE ENTERPRISE LIMITED, Cambridge (GB); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/508,876

(22) PCT Filed: Sep. 4, 2015

(86) PCT No.: PCT/EP2015/070300
§ 371 (c)(1),
(2) Date: Mar. 3, 2017

(87) PCT Pub. No.: WO2016/034728
PCT Pub. Date: Mar. 10, 2016

(65) Prior Publication Data
US 2017/0202779 A1    Jul. 20, 2017

(30) Foreign Application Priority Data
Sep. 4, 2014 (GB) .................................. 1415681

(51) Int. Cl.
*A61K 9/48* (2006.01)
*A61K 9/51* (2006.01)
*B01J 13/08* (2006.01)

(52) U.S. Cl.
CPC .......... *A61K 9/4825* (2013.01); *A61K 9/4833* (2013.01); *A61K 9/5169* (2013.01); *B01J 13/08* (2013.01)

(58) Field of Classification Search
CPC .. A61K 9/4825; A61K 9/5169; A61K 9/4833; B01J 13/08
See application file for complete search history.

(56) References Cited

U.S. PATENT DOCUMENTS

| | | | |
|---|---|---|---|
| 8,501,172 B2 | 8/2013 | Kaplan et al. | |
| 2004/0096852 A1* | 5/2004 | Dobson | C07K 14/4711 435/6.16 |
| 2006/0088476 A1* | 4/2006 | Harder | A61K 49/0419 424/9.411 |
| 2007/0259382 A1 | 11/2007 | Salem | |
| 2009/0004737 A1 | 1/2009 | Borenstein et al. | |
| 2010/0028451 A1* | 2/2010 | Kaplan | A61K 9/1658 424/491 |
| 2010/0029553 A1 | 2/2010 | Scheibel | |
| 2010/0191328 A1 | 7/2010 | Kaplan et al. | |
| 2010/0278883 A1 | 11/2010 | Liebmann et al. | |
| 2011/0116993 A1 | 5/2011 | Nam et al. | |
| 2011/0129941 A1* | 6/2011 | Kumacheva | B01F 5/0647 436/180 |
| 2011/0135697 A1 | 6/2011 | Omenetto et al. | |
| 2011/0280944 A1 | 11/2011 | Stupp et al. | |
| 2013/0136779 A1 | 5/2013 | Scheibel et al. | |
| 2013/0240251 A1 | 9/2013 | Kaplan et al. | |
| 2013/0243693 A1 | 9/2013 | Omenetto et al. | |
| 2014/0023688 A1 | 1/2014 | Budijono et al. | |
| 2014/0045695 A1 | 2/2014 | Liebmann et al. | |
| 2015/0157576 A1* | 6/2015 | Shum | A61K 35/12 424/455 |

FOREIGN PATENT DOCUMENTS

| | | |
|---|---|---|
| CN | 103209991 A | 7/2013 |
| EP | 2021361 B1 | 8/2012 |
| EP | 2349366 B1 | 8/2013 |
| WO | 2005103106 A1 | 11/2005 |
| WO | 2007014755 A1 | 2/2007 |
| WO | 2007057448 A1 | 5/2007 |
| WO | 2007141131 A1 | 12/2007 |
| WO | 2008108838 A2 | 9/2008 |
| WO | 2008148200 A1 | 12/2008 |
| WO | 2012054582 A2 | 4/2012 |
| WO | 2012078760 A1 | 6/2012 |
| WO | 2012145652 A1 | 10/2012 |
| WO | WO-2013014452 A1 * | 1/2013 ............... B82Y 5/00 |

(Continued)

OTHER PUBLICATIONS

T. Yang et al., "Synthesis, Characterization, and Self-Assembly of Protein Lysozyme Monolayer-Stabilized Gold Nanoparticles," Langmuir 2007, 23, 10533-10538.*
Y. Wang et al., "Nanoscale Characterization of Zein Self-Assembly," Langmuir 2012, 28, pp. 2429-2435.*
E. Frare, "Identification of the Core Structure of Lysozyme Amyloid Fibrils by Proteolysis," J. Mol. Biol. (2006) 361, 551-561.*
Allmeling, et al., "Use of spider silk fibres as an innovative material in a biocompatible artificial nerve conduit", J Cell Mol Med 10(3), 770-777 (2006).
Altman, et al., "Silk-based biomaterials", Biomaterials 24, 401-416 (2003).

(Continued)

*Primary Examiner* — Monica A Shin
(74) *Attorney, Agent, or Firm* — James S. Keddie; Bozicevic, Field & Francis LLP

(57) ABSTRACT

The present invention provides capsules having a shell of material that comprises an assembly of a protein, and the capsule is optionally provided with a network of material within the shell that is an assembly of the protein. The assembly of the protein is obtained or obtainable by the aggregation of the protein, optionally together with another protein. The assembly is a non-covalent assembly of a protein.

23 Claims, 14 Drawing Sheets

(56) References Cited

FOREIGN PATENT DOCUMENTS

| WO | 2013070907 A1 | 5/2013 |
|---|---|---|
| WO | 2013071107 A1 | 5/2013 |
| WO | 2013071123 A1 | 5/2013 |
| WO | 2013102193 A1 | 7/2013 |
| WO | 2013103424 A9 | 7/2013 |
| WO | 2013120856 A1 | 8/2013 |
| WO | 2013142119 A1 | 9/2013 |
| WO | 2014118553 A1 | 8/2014 |
| WO | 2016034728 A1 | 3/2016 |

OTHER PUBLICATIONS

Anna, et al., "Formation of dispersions using "flow focusing" in microchannels", Applied Physics Letters 82(3), 364-366 (2003).

Bartus, et al., "Sustained Delivery of Proteins for Novel Therapeutic Products", Science 281, 1161-1162 (1998).

Bell, et al., "Changes in Fine Structure During Silk Protein Production in the Ampullate Gland of the Spider", The Journal of Cell Biology 42, 284-295 (1969).

Booth, et al., "Instability, unfolding and aggregation of human lysozyme variants underlying amyloid fibrillogenesis", Nature 385, 787-793 (1997).

Chin, et al., "Spontaneous assembly of marine dissolved organic matter into polymer gels", Nature 391, 568-572 (1998).

Cole, "Rapid chemosensitivity testing of human lung tumor cells using MTT assay", Cancer Chemother Pharmacol 17, 259-263 (1986).

Diez-Pascual, et al., "Effect of layer-by-layer confinement of polypeptides and polysaccharides onto thermoresponsive microgels: A comparative study", Journal of Colloid and Interface Science 347, 79-89 (2010).

Dobson, et al., "Protein folding and misfolding", Nature 426, 884-890 (2003).

Feng, et al., "Evaluation of FT-IR and Nile Red methods for microalgal lipid characterization and biomass composition determination", Bioresource Technology 128, 107-112 (2013).

Fowler, et al., "Co-operative mineralization and protein self-assembly in amelogenesis: silica mineralization and assembly of recombinant amelogenins in vitro", European Journal of Oral Sciences 114, 297-303 (2006).

Gosline, et al., "The Mechanical Design of Spider Silks: From Fibroin Sequence to Mechanical Function", Journal of Experimental Biology 202, 3295-3303 (1999).

Gu, et al., "Glucose-Responsive Microgels Integrated with Enzyme Nanocapsules for Closed-Loop Insulin Delivery", ACS Nano 7(8), 6758-6766 (2013).

Ha, et al., "Structural Studies of Bombyx mori Silk Fibroin during Regeneration from Solutions and Wet Fiber Spinning", Biomacromolecules 6, 1722-1731 (2005).

Holland, et al., "Silk and Synthetic Polymers: Reconciling 100 Degrees of Separation", Advanced Materials 24, 105-109 (2012).

Holtze, et al., "Biocompatible surfactants for water-in-fluorocarbon emulsions", Lab Chip 8, 1632-1639 (2008).

Hsu, et al., "Thioflavin T and its Photoirradiative Derivatives: Exploring Their Spectroscopic Properties in the Absence and Presence of Amyloid Fibrils", J Phys Chem B 117, 3459-3468 (2013).

Hu, et al., "Shape controllable microgel particles prepared by microfluidic combining external ionic crosslinking", Biomicrofluidics 6, 026502, 9 pages (2012).

Hwang, et al., "Stop-Flow Lithography for the Production of Shape-Evolving Degradable Microgel Particles", J Am Chem Soc 131, 4499-4504 (2009).

Jia, et al., "Hyaluronic Acid-Based Microgels and Microgel Networks for Vocal Fold Regeneration", Biomacromolecules 7, 3336-3344 (2006).

Kesselman, et al., "Synthesis of Monodisperse, Covalently Cross-Linked, Degradable "Smart" Microgels Using Microfluidics", Small 8(7), 1092-1098 (2012).

Knowles, et al., "Nanomechanics of functional and pathological amyloid materials", Nat Nanotechnol 6, 469-479 (2011).

Lammel, et al., "Recombinant spider silk particles as drug delivery vehicles", Biomaterials 32, 2233-2240 (2011).

Langer, et al., "Designing materials for biology and medicine", Nature 428, 487-492 (2004).

Lawrence, et al., "Bioactive Silk Protein Biomaterial Systems for Optical Devices", Biomacromolecules 9, 1214-1220 (2008).

Li, et al., "Biodegradable nanocomposites of amyloid fibrils and graphene with shape-memory and enzyme-sensing properties", Nat Nano 7, 421-427 (2012).

Li, et al., "Hybrid nanocomposites of gold single-crystal platelets and amyloid fibrils with tunable fluorescence, conductivity, and sensing properties", Advanced Materials 25, 3694-3700 (2013).

Li, et al., "Lysozyme Uptake by Oxidized Starch Polymer Microgels", Biomacromolecules 11, 1754-1762 (2010).

Lian, et al., "Monodisperse alginate microgel formation in a three-dimensional microfluidic droplet generator", Biomicrofluidics 6, 044108, 12 pages (2012).

Link, et al., "Electric Control of Droplets in Microfluidic Devices", Angew Chem Int Ed 45, 2556-2560 (2006).

Liu, et al., "Decolorization and biodegradation of remazol brilliant blue R by bilirubin oxidase", Journal of Bioscience and Bioengineering 108(6), 496-500 (2009).

Maji, "Amyloid as a depot for the formulation of long-acting drugs", PLoS Biol 6, e17 (2008).

Nicholson, et al., "A Method for Studying the Structure of Uniaxially Aligned Biopolymers Using Solid State 15N-NMR: Application to Bombyx mori Silk Fibroin Fibers", Biopolymers 33, 847-861 (1993).

O'Brien, et al., "The electrophoretic mobility of large colloidal particles", Can J Chem 59, 1878-1887 (1981).

Paparcone, et al., "Mutations alter the geometry and mechanical properties of Alzheimer's Aβ(1-40) amyloid fibrils", Biochemistry 49, 8967-8977 (2010).

Patent Cooperation Treaty, International Searching Authority, Search Report and Written Opinion for PCT/EP2015/070300, 16 pages, dated Nov. 30, 2015.

Peer, et al., "Nanocarriers as an emerging platform for cancer therapy", Nature Nanotechnology 2, 751-760 (2007).

Porter, et al., "Silk as a Biomimetic Ideal for Structural Polymers", Adv Mater 21, 487-492 (2009).

Pritchard, et al., "Silk fibroin biomaterials for controlled release drug delivery", Expert Opin Drug Deliv 8, 797-811 (2011).

Qin, et al., "Soft lithography for micro- and nanoscale patterning", Nature Protocols 5(3), 491-502 (2010).

Rising, et al., "Spider Silk Proteins—Mechanical Property and Gene Sequence", Zoological Science 22, 273-281 (2005).

Rockwood, et al., "Materials fabrication from Bombyx mori silk fibroin", Nature Protocols 6(10), 1612-1631 (2011).

Sagis, et al., "Polymer Microcapsules with a Fiber-Reinforced Nanocomposite Shell", Langmuir 24, 1608-1612 (2008).

Samal, et al., "Silk Microgels Formed by Proteolytic Enzyme Activity", Acta Biomater 9(9), 8192-8199 (2013).

Santos, et al., "Ultrasonication of insulin-loaded microgel particles produced by internal gelation: Impact on particle's size and insulin bioactivity", Carbohydrate Polymers 98, 1397-1408 (2013).

Search Report, for Applicaton No. GB1415681.4, 4 pages, dated May 26, 2015.

Seiffert, et al., "Janus Microgels Produced from Functional Precursor Polymers", Langmuir 26(18), 14842-14847 (2010).

Shimanovich, et al., "Encapsulation of RNA Molecules in BSA Microspheres and Internalization into Trypanosoma Brucei Parasites and Human U2OS Cancer Cells", Adv Funct Mater 21, 3659-3666 (2011).

Sipe, et al., "Amyloid fibril protein nomenclature: 2010 recommendations from the nomenclature committee of the International Society of Amyloidosis", Amyloid, 17(3-4), 101-104 (2010).

Suh, et al., "Synthesis of Nonspherical Superparamagnetic Particles: In Situ Coprecipitation of Magnetic Nanoparticles in Microgels

(56) References Cited

OTHER PUBLICATIONS

Prepared by Stop-Flow Lithography", J Am Chem Soc 134, 7337-7343 (2012).

Tao, et al., "Silk-Based Conformal, Adhesive, Edible Food Sensors", Adv Mater 24, 1067-1072 (2012).

Teule, et al., "A protocol for the production of recombinant spider silk-like proteins for artificial fiber spinning", Nat Protoc 4(3), 341-355 (2009).

Toshiki, et al., "Germline transformation of the silkworm *Bombyx mori* L. using a piggyBac transposon-derived vector", Nature Biotechnology 18, 81-84 (2000).

Uversky, et al., "Conformational constraints for amyloid fibrillation: the importance of being unfolded", Biochimica et Biophysica Acta 1698, 131-153 (2004).

Vepari, et al., "Silk as a Biomaterial", Prog Polym Sci 32(8-9), 991-1007 (2007).

Vollrath, et al., "Liquid crystalline spinning of spider silk", Nature 410, 541-548 (2001).

Wang, et al., "Exploring a direct injection method for microfluidic generation of polymer microgels", Lab Chip 13, 2547, 7 pages (2013).

Wang, et al., "Silk microspheres for encapsulation and controlled release", Journal of Controlled Release 117(3), 360-370 (2007).

Wang, et al., "Stem cell-based tissue engineering with silk biomaterials", Biomaterials 27, 6064-6082 (2006).

Wang, et al., "The Intrinsic Ability of Silk Fibroin to Direct the Formation of Diverse Aragonite Aggregates", Adv Funct Mater 22, 435-441 (2012).

Yang, et al., "Microfluidic assisted synthesis of multi-functional polycaprolactone microcapsules: incorporation of CdTe quantum dots, Fe3O4 superparamagnetic nanoparticles and tamoxifen anti-cancer drugs", Lab Chip 9, 961-965 (2009).

Zhang, "Applications of natural silk protein sericin in biomaterials", Biotechnology Advances 20, 91-100 (2002).

Zhang, "Fabrication of novel biomaterials through molecular self-assembly", Nat Biotech 21, 1171-1178 (2003).

Rambaran et al., "Amyloid fibrils: abnormal protein assembly", Prion, 2008, 2(3): 112-117.

\* cited by examiner

Figure 1
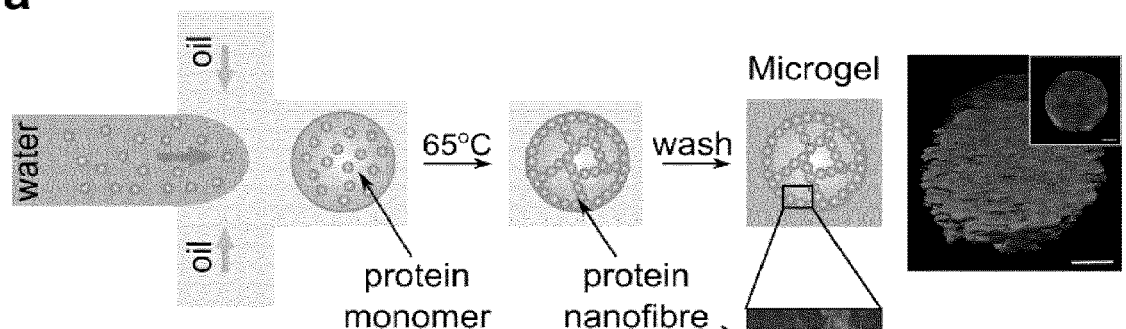
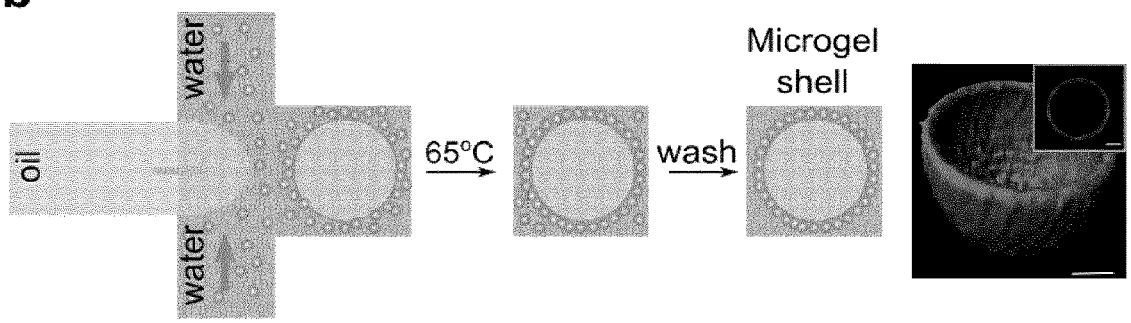
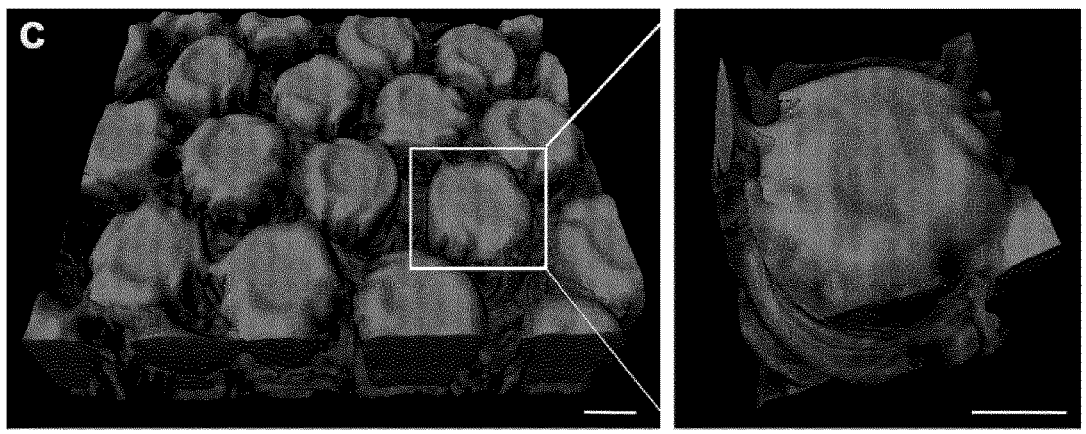
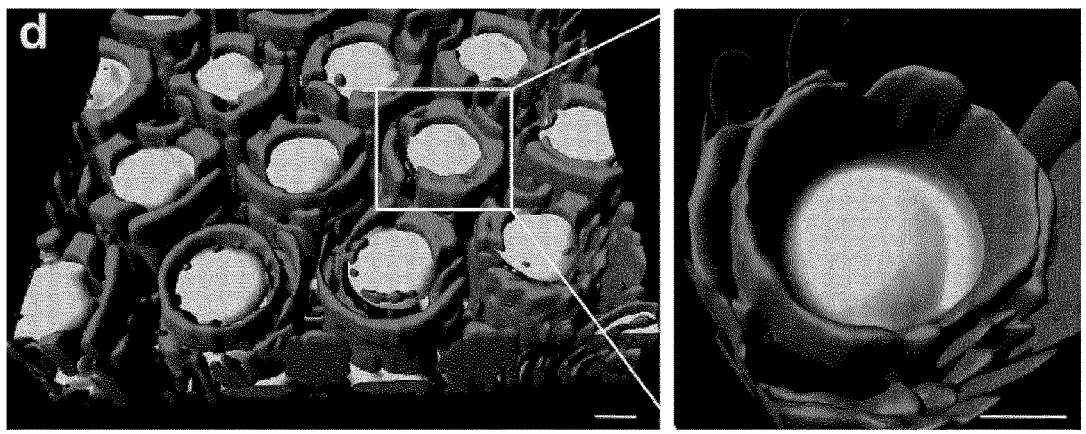

*Figure 3*
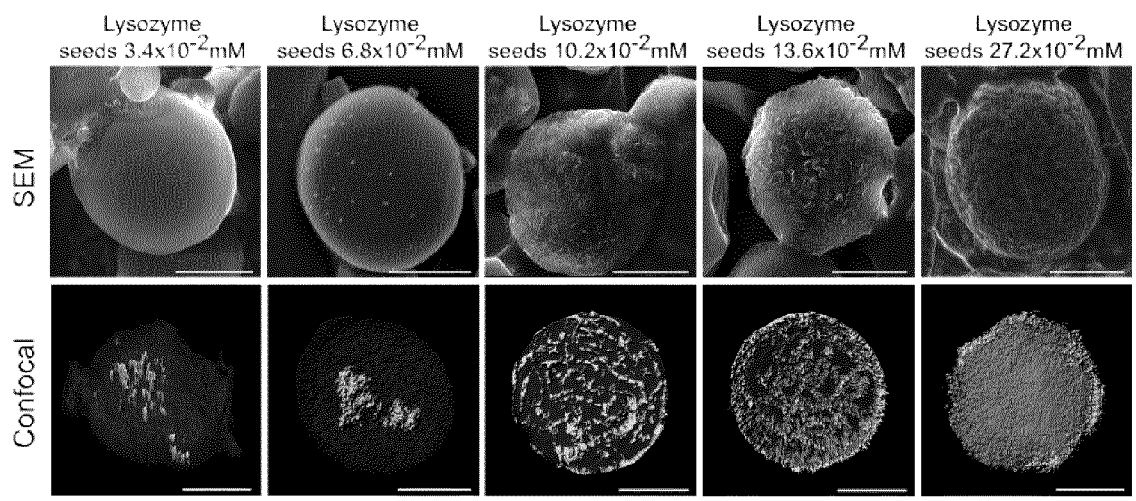
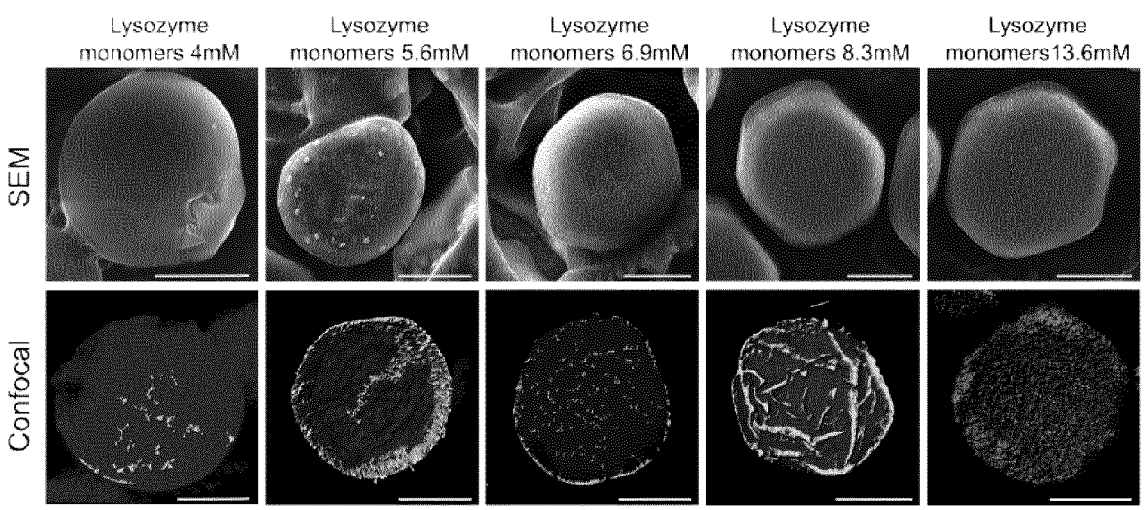

Figure 4 (a) - (c)
a
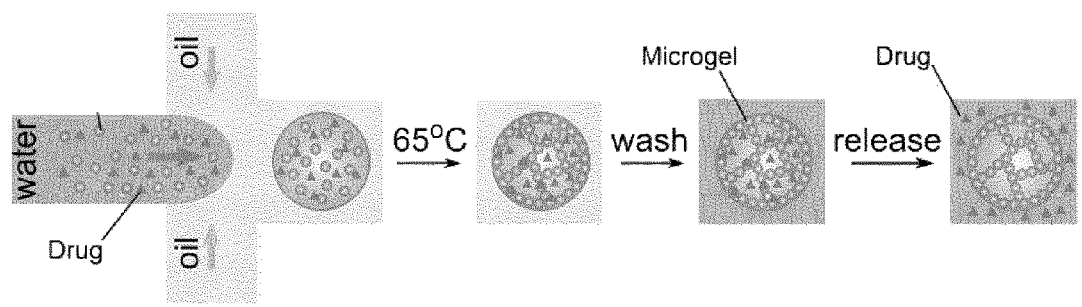
b
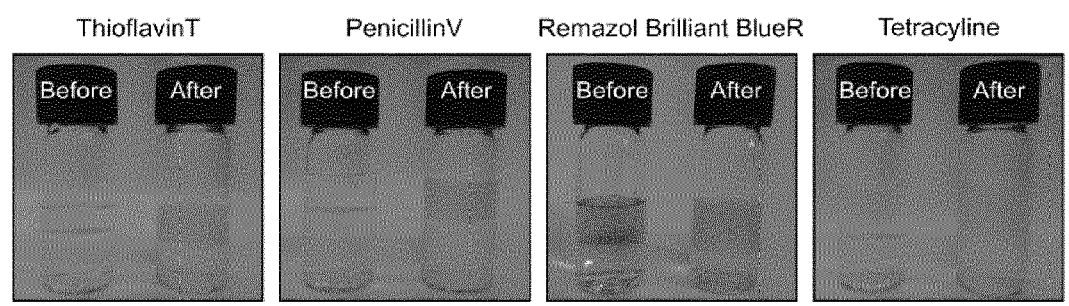
c
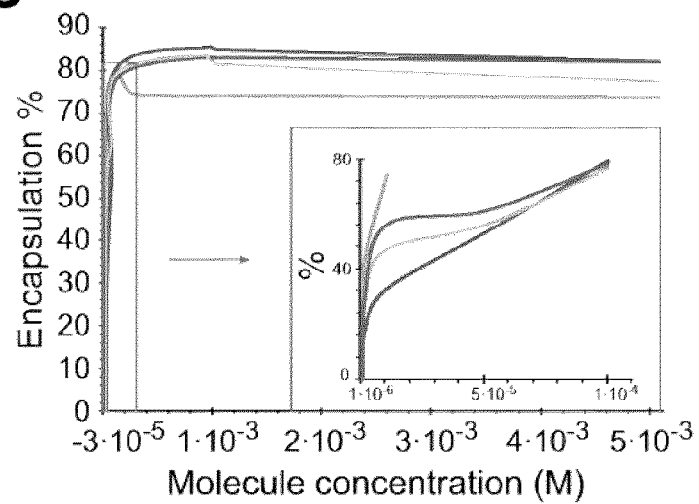

Figure 4 (d) - (e)
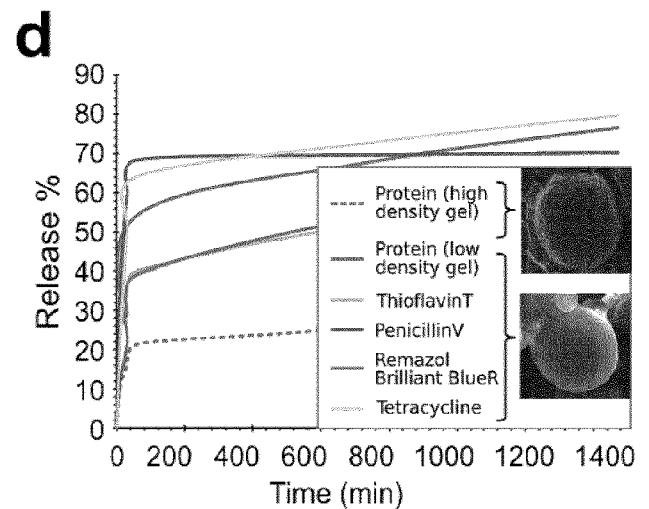
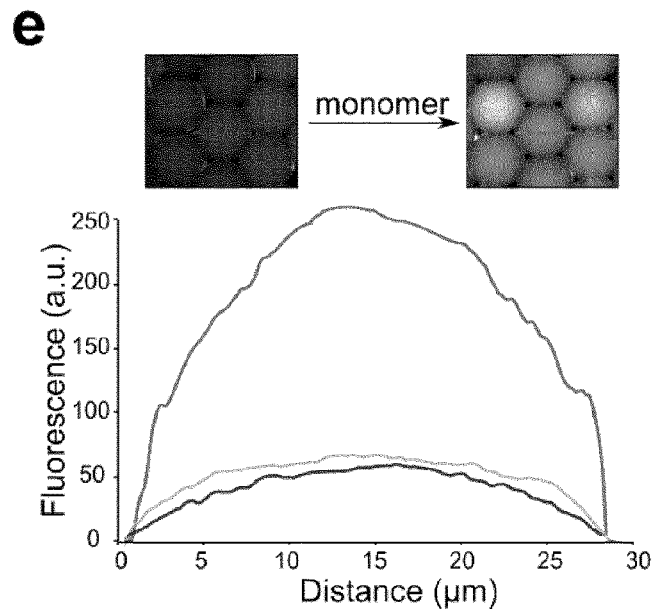
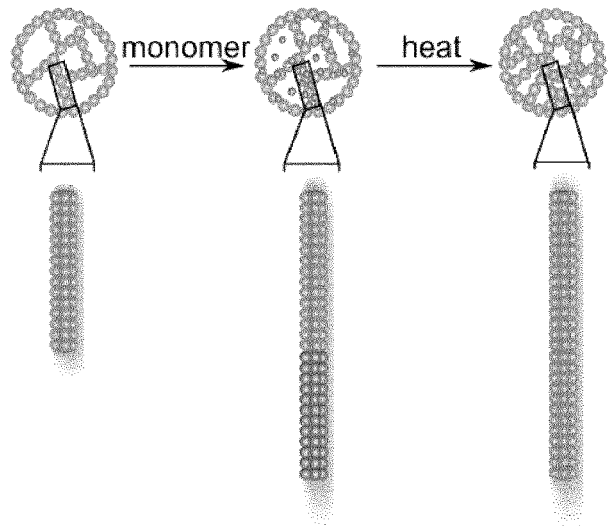

*Figure 5*
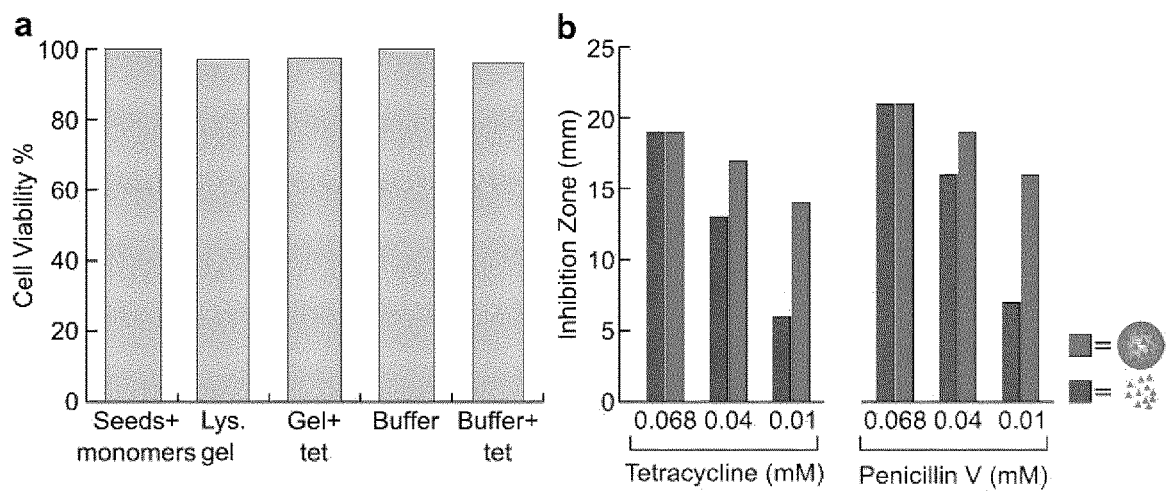
*Figure 6*
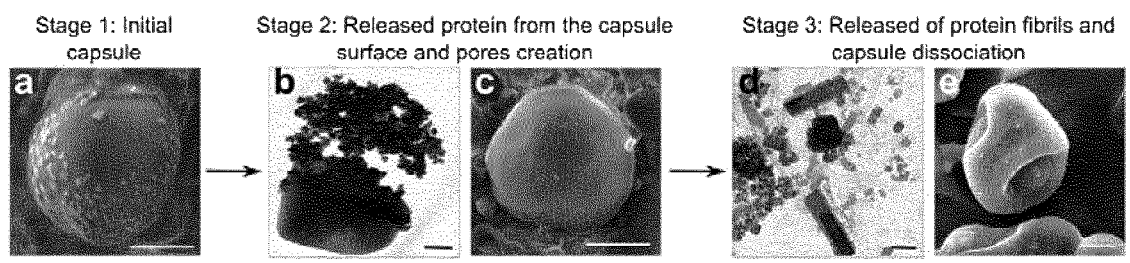
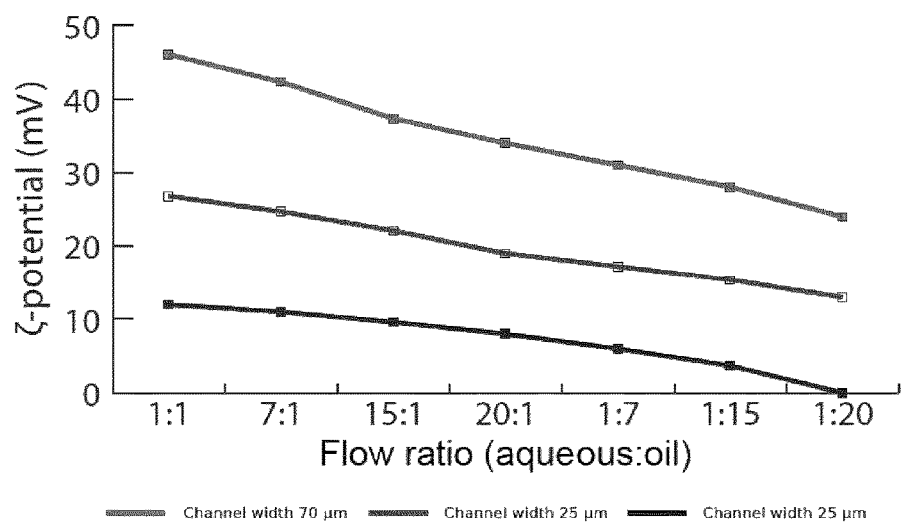

Figure 8
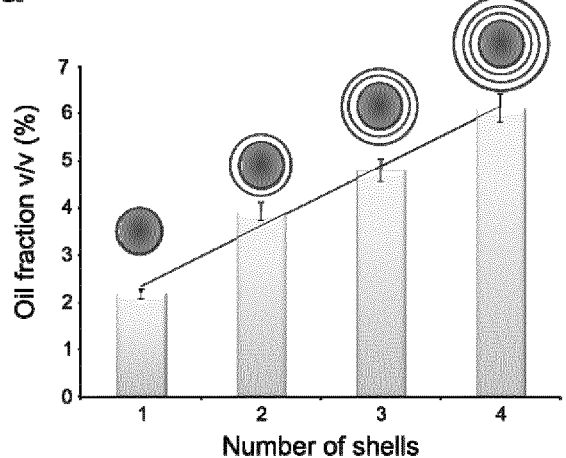
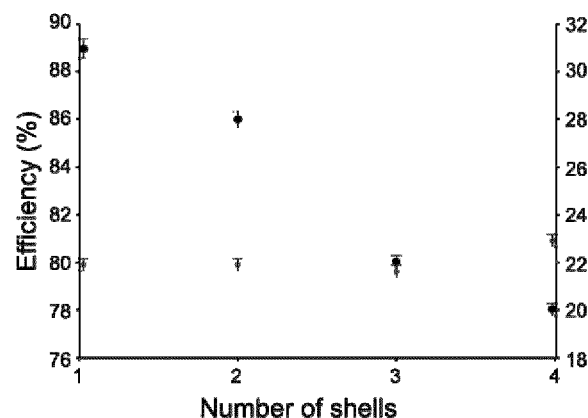
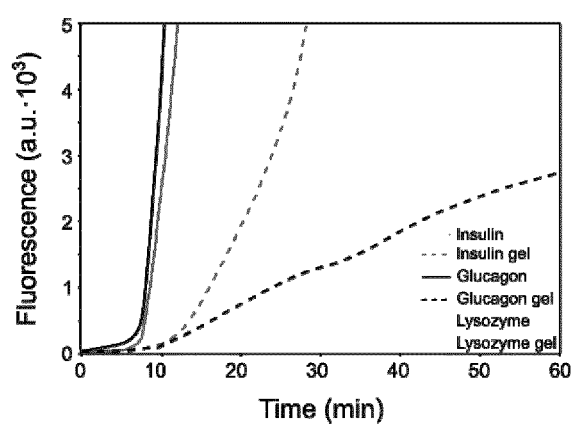
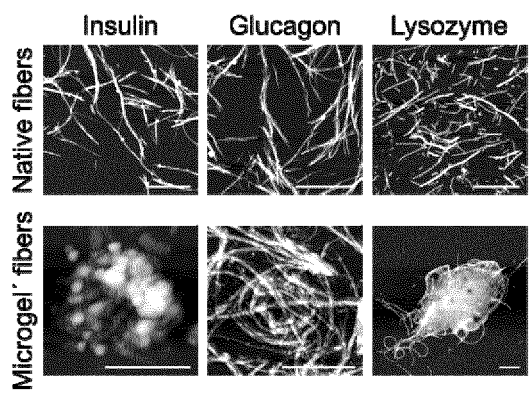

Figure 9
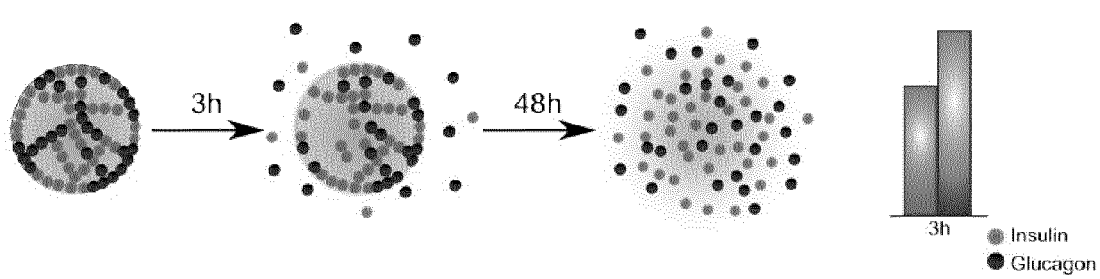
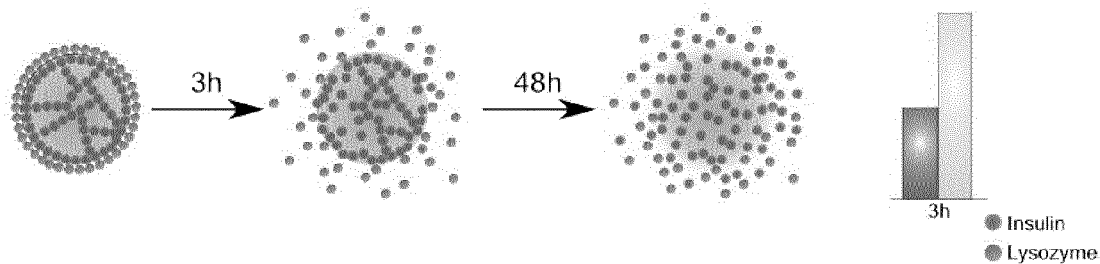
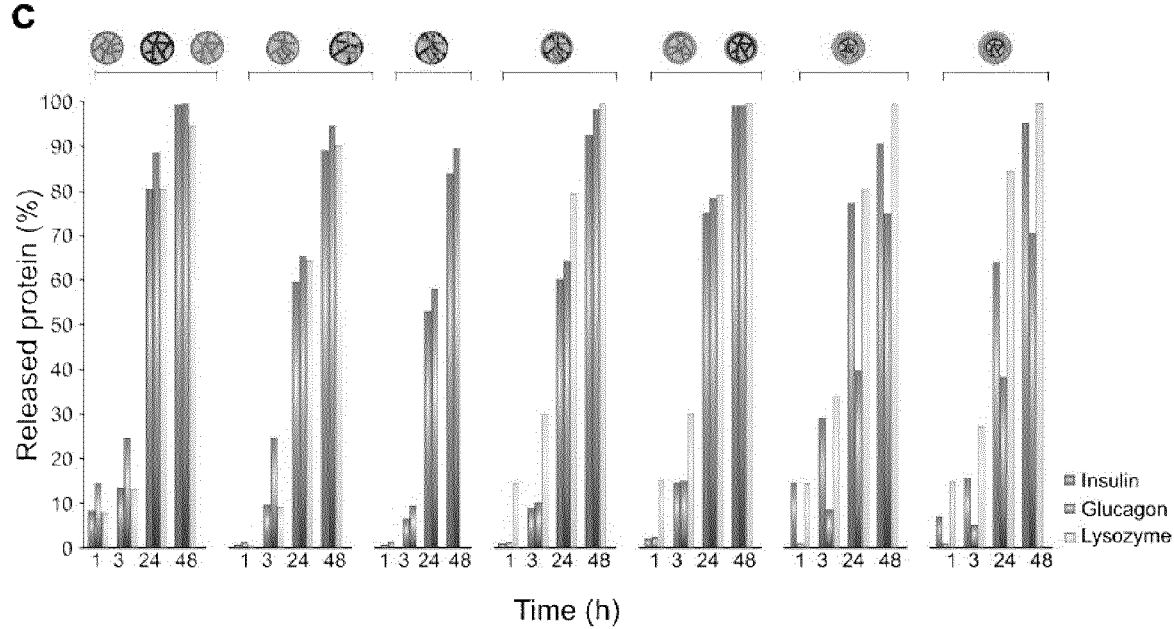

*Figure 12*

| Material | TEM image | Crystalinity | Diffraction d-spacing (Å) | Crystal structure |
|---|---|---|---|---|
| Lysozyme protein seeds | 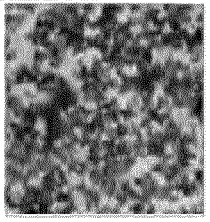 | Crystalline | 1) 2.73<br>2) 1.62<br>3) 1.34 | Tetragonal |
| Lysozyme protein | 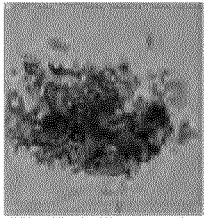 | Amorphous | Amorphous | Amorphous |
| Lysozyme capsule | 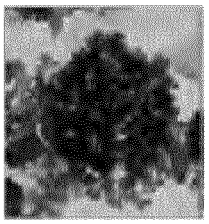 | Crystalline | 1) 2.57<br>2) 1.53<br>3) 1.46 | Tetragonal |
| Dissociated lysozyme capsule | 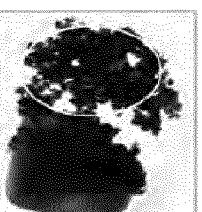 | Crystalline | 1) 2.58<br>2) 1.57<br>3) 1.45 | Tetragonal |
| Dissociated lysozyme capsule |  | Amorphous | Amorphous | Amorphous |
| Released lysozyme fibrills | 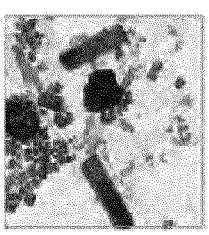 | Amorphous | Amorphous | Amorphous |

PROTEIN CAPSULES

RELATED APPLICATION

This application is a 35 U.S.C. § 371 International Application No. of PCT/EP2015/070300, filed on 4 Sep. 2015, which claims the benefit of priority of GB Application No. 1415681.4 filed on 4 Sep. 2014 (04/09/2014), the contents of which are hereby incorporated by reference in their entirety.

FIELD OF THE INVENTION

This invention relates to capsules, particularly microcapsules, based on a network of an assembled protein, and methods for the preparation of such capsules, and their use in methods of delivering encapsulated components.

BACKGROUND

Amyloid fibrils are linear protein structures, initially recognised in the context of pathology as the hallmark of protein misfolding diseases, but more recently discovered as the basis of numerous functional materials in nature, including catalytic scaffolds and bacterial coatings. Due to their robust material properties (Knowles et al. *Nat. Nanotechnol.* 6, 469-479 (2011); Paparcone et al. *Biochemistry* 49, 8967-8977 (2010)) and ability to self-assemble accurately from a range of proteins and peptides (Fowler et al. *European Journal of Oral Sciences* 114, 297-303 (2006); Li et al. *Nat. Nano* 7, 421-427 (2012); Li et al. *Advanced Materials* 25, 3694-3700 (2013)), artificial variants of these nanoscale materials are finding increasing use as cell culture scaffolds and drug delivery vehicles (Zhang et al. *Nat. Biotech.* 21, 1171-1178 (2003); Maji, S. K. et al. *PLoS Biol.* 6, e17 (2008)).

However, these applications of the general amyloid scaffold are limited by the challenge in controlling the overall micron scale morphology to progress beyond spatially uniform gels.

The present inventors have found that a protein may be self-assembled under controlled conditions to form structures with discrete morphologies.

SUMMARY OF THE INVENTION

In a general aspect the present invention provides capsules having a shell of material that comprises an assembly of a protein, and the capsule is optionally provided with a network of material within the shell that is an assembly of the protein. The assembly of the protein is obtained or obtainable by the aggregation of the protein, optionally together with another protein. The assembly is a non-covalent assembly of a protein.

The capsules of the present invention may be regarded as microgels, such as hydromicrogels. These structures are easy to synthesise, biodegradable and non-toxic and are suitable for encapsulation and releasing components, such as small molecules.

The protein is typically provided as an assembly that has an amyloid fibril form. The capsules of the invention are substantially free of oligomeric forms of the protein. Oligomeric structures are associated with potentially toxic effects, and the protein aggregation methods described herein allow such structures to be avoided. As described herein an oligomer may comprise from 2-50 proteins. Such structures have a considerably lower combined molecular weight than the amyloid fibril form.

Accordingly in a first aspect of the invention there is provided a capsule having a shell of material that comprises an assembly of a protein, such as a fibril assembly of the protein.

The shell is obtained or obtainable from the self-assembly of the protein. In one embodiment, the shell is obtainable from the self-assembly of two or more proteins. The assembly is a non-covalent assembly of the protein.

In one embodiment, the capsule further comprises a network within the shell that comprises an assembly of the protein. In other embodiments, the capsule comprises a protein that is held with the shell of the capsule. Such a protein is not necessarily in an assembled form, and the capsule may be regarded as encapsulating that protein.

In one embodiment, the network comprises fibrils of protein.

In one embodiment, the shell and the network are connected.

In a second aspect of the invention there is provided a capsule holding a component, wherein the capsule is a capsule of the first aspect of the invention.

In a third aspect of the invention there is provided a method for the preparation of a capsule having a shell that comprises an assembly of a protein, wherein the method comprises the step of:
  (i) contacting a flow of a first phase and a flow of a second phase in a channel, thereby to generate in the channel a dispersion of discrete regions, preferably droplets, of the second phase in the first phase, wherein one of the first and second phases comprises a protein suitable for forming an assembly of proteins, thereby to form a capsule shell at the boundary of the discrete region, wherein the first and second phases are immiscible.

In one embodiment, the protein is provided together with a seed for the assembly of the protein, wherein the seed is an assembly of proteins. The use of a seed may beneficial, for it may promote the protein fibrillation during the capsule forming step.

In one embodiment, the protein is provided in a flow that is an aqueous phase. The aqueous phase may be the first or the second phase.

In one embodiment, the first phase is an aqueous phase. In this embodiment, the capsule formed has a shell of material that is an assembly of proteins.

In one embodiment, the second phase is an aqueous phase. In this embodiment, the capsule formed has a shell of material that is an assembly of proteins and the capsule has a network of material within the shell that comprises an assembly of proteins.

In one embodiment, one of the first and second phases is an aqueous phase, and the other of the first and second phases is a non-aqueous phase. The non-aqueous phase may be an oil phase, including a fluorinated oil phase.

In one embodiment, the second phase comprises a component for encapsulation, and the step (i) provides a capsule having a shell encapsulating the component.

In one embodiment, step (i) includes heating the discrete region, thereby to form a capsule shell at the boundary of the discrete region.

In one embodiment, the method further comprises the subsequent step of (ii) collecting the outflow from the channel, thereby to obtain a droplet, which has a capsule. This step may be performed before or after the heating step.

In a fourth aspect of the invention there is provided a method for modifying a capsule of the first aspect of the invention, the method comprising the steps of:

(i) providing a capsule having a shell according to the first aspect of the invention;
(ii) contacting the capsule with a protein;
(iii) permitting the protein to participate in the assembly with the assembly of proteins at the shell and/or optionally to participate in the assembly of proteins in the network of material, where present.

In one embodiment, the capsule for use in step (i) is obtained or obtainable from the method of the third aspect of the invention. In one embodiment, the method is performed subsequent to the method of the third aspect.

In a further aspect there is provided a method of delivering a component to a location, the method comprising the steps of:
(i) providing a capsule having a shell encapsulating a component, according to the second aspect of the invention;
(ii) delivering the capsule to a target location;
(iii) releasing the component from the shell.

In a further aspect of the invention there is provided a capsule of the first aspect of the invention which is a first capsule, and the first capsule is held within a second capsule, and the second capsule has a shell of material that comprises an assembly of a protein.

The protein in the shell of the first capsule may be different to the protein in the shell of the second capsule.

DESCRIPTION OF THE FIGURES

FIG. 1 includes a schematic representation of protein capsule synthesis: (a) water-in-oil capsules; and (b) oil-in-water capsules. The corresponding 3D confocal images of capsules stained with Nile Red dye are shown on the right hand side of each scheme. Figures (c) and (d) are 3D reconstructions of the confocal images for (c) lysozyme water-in-oil and (d) oil-in-water system. The capsules were stained with Nile Red dye. Red emission (excitation at 594 nm/emission at 617 nm) was observed for the aqueous protein component while green emission (excitation at 488 nm/emission 519 nm) is detected for the oil environment. Scale bars=5 µm.

FIG. 3 are scanning electron microscopy and confocal microscopy images of: (a) SEM images (top) of lysozyme capsules synthesised with an initial seed concentration of $3.4 \times 10^{-2}$ mM and a concentration of soluble protein of 4:08 mM, from left to right: seed concentration increased from $3.4 \times 10^{-2}$ mM to $27.2 \times 10^{-2}$ mM. 3D reconstructions of confocal microscopy images (bottom) of the ThT-stained lysozyme capsule synthesised with an initial seed concentration of $3.4 \times 10^{-2}$ mM and concentration of soluble lysozyme of 4.08 mM, from left to right: with seeds concentration increased from $3.4 \times 10^{-2}$ mM to $27.2 \times 10^{-2}$ mM. The concentrations are indicated on the top of each image; (b) SEM and confocal images of the ThT stained capsule with increasing lysozyme concentration from 4.08 mM to 13.6 mM. The blue emission (excitation 350 nm/emission 438 nm) is detected for lysosome protein monomers, green fluorescent emission (excitation 450 nm/emission 482 nm) detected for lysozyme nanofibrils. Scale Bars=1 µm.

FIG. 4 shows (a) a schematic representation of a small molecule encapsulation into and release from a lysozyme capsule; (b) images of the precursor solutions containing a drug ("before") and the drug loaded capsules ("after"); (c) a graph showing the change in loading efficiency recorded as a function of small molecule concentration; (d) a graph showing the release kinetics (proportion of total amount of molecule released) as a function of time; and (e) fluorescence intensity profiles for the lysozyme gels before (blue) and after (red) incubation with protein monomer solution. The images of corresponding gels are shown above the graph. Figure (e) also shows a schematic representation of post-synthesis modification of a capsule using an introduced monomer (such as lysozyme).

FIG. 5 shows the results of (a) a viability test with U2OS human cells. Cell viability was measured for the following solutions: precursor mixture of lysozyme seeds and lysozyme monomers, lysozyme capsules, lysozyme capsules loaded with tetracycline drug, washing buffer from empty lysozyme capsules and washing buffer from tetracycline loaded lysozyme capsules; and (b) an antibacterial test, where the antibacterial activity of released tetracycline and penicillin V was tested against *S. areus*. Inhibition zones obtained by exposure to the free drug in solution and to the drug encapsulated within lysozyme capsules were measured as a function of concentration. Blue columns represent the free drug and green columns the drug released from capsules.

FIG. 6 is a representation of the release mechanism for lysozyme capsules where (a) is a SEM image of a lysozyme capsule; (b) TEM image of a lysozyme capsule with protein layer detached from the surface. Scale bar=1 µm; (c) SEM image of the capsule illustrating the creation of the pores on the surface; (d) TEM image of lysozyme fibrils released from the capsule. Scale Bar=0.1 µm; and (e) SEM images of disaggregated lysozyme capsule. Scale bars for SEM images=10 µm. At bottom is a graph showing the change in a lysozyme capsule ζ-potential as a function of change in microfluidic channel width and with the change in the ratio of aqueous solution:oil.

FIG. 8 shows (a) a chart representing the increase in oil fraction trapped between the protein shell layers due to an increase in the number of protein shells in a microdroplet; (b) a graph showing the change in the efficiency of capsule formation (in red) and average size of resulted capsules (in blue) as a function of change in number of protein shells in micro droplets; (c) the change in fluorescence (aU) over time in a ThT-based aggregation kinetics study of insulin, glucagon and lysozyme proteins during formation of fibers (solid lines) and capsules (microgels; dashed lines), where the assemblies are, from left to right at 1 a.u., glucagon, insulin, lysozyme, lysozyme, insulin and glucagon; and (d) Atomic Force Microscopy (AFM) images of insulin, glucagon and lysozyme fibrils in native state and capsule form. Scale Bars=200 nm.

FIG. 9 shows a schematic representation of protein release from (a) a mixed insulin and glucagon capsule; (b) a double shell insulin-lysozyme gel, where insulin is localised in the core of the gel particle, while lysozyme is localised in the particle shell; and (c) bar graphs showing the percentage of released protein from eleven capsules, where, from left to right the capsules are insulin capsules; glucagon capsules; lysozyme capsules; mixed lysozyme and insulin capsules; mixed lysozyme and glucagon capsules; mixed insulin and glucagon capsules; double shell capsules, where glucagon and insulin are localised in the core and lysozyme is localised in the particle shell; double shell capsules, where insulin is localised in the core and lysozyme is localised in the particle shell; double shell capsule, where glucagon is localised in the core and lysozyme is localised in the particle shell; The amount of released protein was calculated as a fraction (%) of total proteins introduced into the capsule structure. Each protein was detected following the fluorescent signals: insulin exit. 593 nm/emiss. 614 nm, glucagon excit. 347 nm/emus. 448 nm and lysozyme excit. 490 nm/emiss. 515 nm.

FIG. 12 is a summary of crystal structure and TEM images of lysozyme during the release of lysozyme.

DETAILED DESCRIPTION OF THE INVENTION

Figure 2:
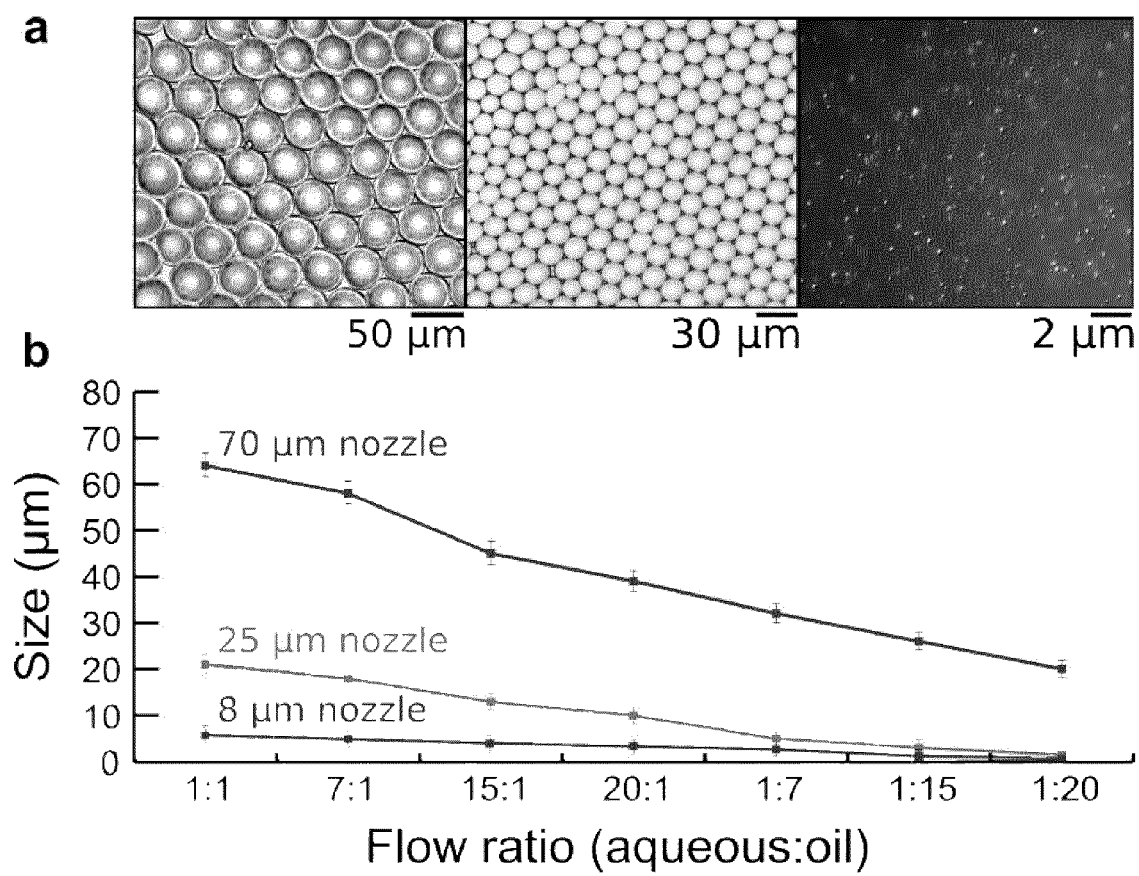
FIG. 2 includes (a) light microscopy images of lysozyme capsules of different sizes (from left to right: 49 µm, 23 µm and 0.34 µm diameter; and (b) a graph showing the change in lysozyme capsule size as a function of change in microfluidic channel width and change in the ratio of aqueous solution to oil flow rates.

The present inventors have established that capsules may be prepared having a shell that is obtainable from the assembly of a protein. The capsules are formed using fluidic droplet generation techniques, amongst others, and the methods of preparation make use of a protein's ability to self-assemble. The ability of a protein to form a discrete shell is surprising given the previously reported behaviour of proteins, which often form amorphous assemblies.

The capsule is obtainable through the use of fluidic droplet preparation techniques. These techniques are particularly beneficial in that they generate droplets having a very low distribution of sizes, which results in capsules having a very low distribution in sizes. Moreover, the methods of the invention allow close control over the formation of the product capsule. Simple changes in the fluidic droplet preparation technique, such as changes in flow rates, may be used to control the size and nature of the capsule obtained, the size of the pores in the shell, and the thickness of the shell, amongst others.

The capsules of the invention are shown to be robust, and are capable of withstanding temperatures of at least 60° C., such as at least 100° C. The capsules also maintain their integrity at reduced pressure.

The capsules of the invention are suitable for encapsulating a component. Using the fluidic droplet preparation techniques described herein, a capsule shell may be constructed in the presence of the component to be encapsulated. Thus, in one procedure the shell may be formed and the component encapsulated. Advantageously therefore, the capsule may be constructed without the need for a later passive diffusion step after the capsule construction. Furthermore, the method of encapsulation allows high rates of incorporation of the material into the capsule, and material waste is therefore minimised.

The invention is now described in more detail with reference to the each feature of the invention.

The capsules of the invention may be referred to as microgels, for example hydromicrogels, where they are provided holding and within a fluid, such as water.

Microgels combine characteristics from two key classes of soft matter, colloids and polymers, and consist of micron scale particles composed of cross-linked polymer networks that behave as a gel (Wei-Chun Chin et al. *Nature* 391, 568-572 (1998); Jia, X. et al. *Biomacromolecules* 7, 3336-3344 (2006); Seiffert et al. *Langmuir* 26, 14842-14847 (2010)). Their ability to respond to environmental stimuli has led to significant efforts to exploit microgels as functional materials. Besides applications for purposes such as nanoparticle synthesis (Suh et al. *J. Am. Chem. Soc.* 134, 7337-7343 (2012)), microgels have been found to be uniquely suited as agents for drug delivery, as they can be loaded with therapeutic agents and can transport the agents across biochemical barriers to release them in specifically targeted tissues (Bartus et al. *Science* 281, 1161-1162 (1998); Peer et al. *Nat. Nano.* 2, 751-760 (2007)).

The majority of microgels described in the literature are synthesised from artificial biocompatible polymers or polysaccharides (Wang et al. Lab Chip 13, 2547 (2013); Diez-Pascual et al. *J. Colloid Interface Sci.* 347, 79-89 (2010)). In the present work the inventors demonstrate a general strategy for the synthesis of microgels (or capsules) from naturally occurring proteins driven by their assembly into nanoscale amyloid filaments, for example under suitable denaturing conditions.

The present application describes a general approach for generating capsules that are composed entirely of proteins. The compartmentalisation of a protein in capsule form may be by the use of droplet microfluidics, and formation of the capsule shell is mediated through the self-assembly of the protein into a network of entangled amyloid fibrils.

This approach is a convenient route to generate solvent-filled capsules having a network of material within, as well capsules having an assembly of proteins only at the capsule shell. The methods of the invention allow for the encapsulation of a variety of both hydrophilic and hydrophobic small molecules into the capsules.

As shown herein, protein capsules are non-toxic to human cell lines. The capsules are effective at encapsulating drug molecules, and they may be used for the local release of those drugs, which provides for an enhanced pharmacological action, as exemplified through the use of two common antibiotics.

In addition, the capsules are dynamic materials whose structure, such as the internal structure, may be altered in response to its exposure to monomeric protein.

Due to their biocompatibility, self-assembling dynamic nature and effective delivery characteristics, the capsules of the invention represent a promising new class of structured protein materials.

Sagis et al. have previously described polymer microcapsules having a nanocomposite shell. The shell consists of alternating layers of pectin and whey protein fibrils. The microcapsules are prepared by electrostatic layer-by-layer absorption of protein material onto oil droplets. The use of flow methods for the preparation of capsule is not described. The nature of the interaction between proteins is not disclosed.

US 2014/0023688 relates to methods of making silk particles including sonication of silk in a water in oil emulsion, and silk in an oil in water in oil emulsion.

US 2013/0136779 describes nano- and microcapsules made from spider silk. This document describes the assembly of colloidal particles made from spider silk proteins at the oil and water interface.

US 2011/0280944 discloses microcapsules formed from peptide amphiphiles and biopolymers which assemble when nebulized.

WO 2013/120856 explains that that spontaneous nanoparticles can be formed by mixing a water miscible non-volatile organic solvent, such as propylene glycol, with a vegetable hydrophobic protein non-solvent, such as zein.

Capsules

A capsule of the invention comprises a shell. The shell is a network that is formed from the self-assembly of a protein. The shell defines an internal space, which is suitable for holding a component. Thus, in one embodiment, the capsules of the invention extend to those capsules encapsulating a component within the shell. The shell may form a barrier limiting or preventing the release of material encapsulated within.

In one embodiment, the internal space defined by the shell may be regarded as a hollow space which is substantially free of protein in an assembled from. Thus, an assembly of proteins is present as the shell.

In other embodiments of the invention, the shell internal space comprises a network of material within the shell that is an assembly of the protein. This network is preferably connected to the shell and is contiguous with the assembly of the protein that forms the shell. Here, the capsule may take on the form of a gel particle.

Where the network is present, the internal space of the shell may retain its ability to hold a component within. Thus, the network does not substantially occupy the entire internal space.

In an alternative embodiment, the network occupies substantially the entire internal space of the capsule. Thus the internal space may be regarded as having a dense, optionally substantially solid, fibrillar protein content.

In one embodiment, the capsule holds water within the shell. The water may be an aqueous solution comprising the protein and optionally the seed that are used in the preparation of the capsule shell. As noted above, in some embodiments, the shell holds a network of material that is an assembly, such as a fibril, of proteins. Where the capsule holds water within its shell it may be referred to as a hydrogel, such as a hydromicrogel.

Within the shell there may be provided an encapsulated material, which may be provided in addition to water and the reagents that are for use in the supramolecular assembly of the shell.

In one embodiment, the capsule holds a non-aqueous phase within the shell. Within the shell there may be provided an encapsulated material.

Where the capsule is said to encapsulate a component, it is understood that this encapsulated component may be present within the internal space defined by the shell. In one embodiment, the encapsulant is also present, at least partially, within the pores of the shell.

A component held in a shell may be releasable from the capsule, through pores that are present in the shell. In some embodiments, the pores are sufficiently small to prevent the component from being released. Thus, the assembly of proteins making up the shell may be at least partly disassembled thereby permitting release of material from within the shell.

The presence of a component within the shell and/or within the pores of the shell may be determined using suitable analytical techniques which are capable of distinguishing the shell material and the encapsulant. For example, each of the shell material and the component may have a detectable label or suitable functionality that is independently detectable (orthogonal) to the label or functionality of the other. In one embodiment, each of the shell and the component has an orthogonal fluorescent label. For example, one has a rhodamine label and the other has a fluorescein label. Laser scanning confocal microscopy techniques may be used to independently detect the fluorescence of each label, thereby locating each of the shell and encapsulant. Where the component signals are located at the same point as the signals from the shell, it is understood that the component resides within a pore of the shell.

Other labels, such as Nile Red dye and ThT may be used to stain the assembly of proteins. These compounds may be used to label the capsule after its formation. Dyes, such as ThT are well known to bind to amyloid fibrils and are therefore useful for labelling the assembly of the protein that is present in the capsules of the present case.

The general shape of the shell, and therefore the shape of the capsule, is not particularly limited. In practice however, the shape of the capsule may be dictated by its method of preparation. In the preparation methods described herein, a capsule shell may be prepared using fluidic droplet formation techniques. Typically, the shell material is formed at the boundary of a discrete (or discontinuous) phase in a continuous phase. For example, one phase may be an aqueous phase, and the other may be a water immiscible phase. The discrete region may be a droplet, having a substantially spherical shape. The shell formed is therefore also substantially spherical.

Adaptations to the fluidic conditions allow for the formation of discrete regions that are not spherical. For example, the discrete region may take the form of a slug.

In certain embodiments, a capsule may be obtained when the shell has a substantially spherical shape. This capsule may be subjected to a drying step, which reduces the amount of solvent (for example, water) in and around the capsule. As a result of this step, the capsule shrinks in size. At first the shell maintains a substantially spherical shape. After further drying, the capsule sphere may partially or fully collapse in on itself. The structural integrity of the capsule is maintained and the shell simply distorts to accommodate changes in the internal volume. Thus, the capsules of the invention include those capsules where the shell is an at least partially collapsed sphere.

Given the formation of the capsule shell at the boundary of the discrete region (for example, a droplet), references to the dimensions of a droplet may also be taken as references to the dimension of the capsule. The capsule shell may form prior to a drying step.

The inventors have established that capsules that have been shrunk, for example by desolvation, may subsequently be returned to their original substantially spherical shape, by, for example, resolvating the capsule. The worked examples provided in the present case show such changes to the capsule.

The shape of a capsule may be determined by simple observation of the formed capsule using microscopy, such as light microscopy, scanning electron microscopy or confocal microscopy. Where the shell material comprises a label, the detection of the label through the shell will reveal the capsule shape. For example, where the label is a fluorescent label, laser scanning confocal microscopy may be used to locate the shell material and its shape.

The size of the capsule is not particularly limited. In one embodiment, a capsule is a microcapsule or a nanocapsule.

In one embodiment, each capsule has an average size of at least 0.1, 0.2, 0.5, 0.6, 0.7, 1, 5, 10, 20, 30, 40, 50, 100 or 200 μm in diameter.

In one embodiment, each capsule has an average size of at most 400, 200, 100, 75, 60 or 50 μm in diameter.

In one embodiment, the capsule size is in a range where the minimum and maximum diameters are selected from the embodiments above. For example, the capsule size is in range from 0.6 to 60 μm in diameter.

Average size refers to the numerical average of measured largest cross section, such as diameter, for a sample of capsules. Typically, at least 5 capsules in the sample are measured. A cross section measurement is taken from the outmost edges of the shell.

The cross-section of a capsule may be determined using simple microscopic analysis of the formed capsules. For example, the formed capsules may be placed on a microscope slide and the capsules analysed. Alternatively, the capsule size may be measured during the preparation process, for example as the capsules are formed in a channel of a fluidic device (i.e. in line).

The measurement of the cross section may also be achieved using techniques related to the detection of a detectable label that is associated with capsule shell, or functionality present within the shell material. As mentioned above in relation to detection and location of the encapsulated component, the shell material may comprise a fluorescent label which may be detected by laser scanning confocal microscopy techniques or the shell material may be labelled with a label that is bound to the shell after capsule formation. The presence of multiple labels within and around the capsule shell allows the cross-sectional shape to be determined, and the largest cross-section measured.

In the preparation method described herein a capsule is prepared using a fluidic droplet generation technique. The capsule shell is formed in a droplet, which is created in a channel of a fluidic droplet generating device, at the boundary of the aqueous phase of the droplet with the continuous phase. The size of the capsule is therefore substantially the same as that of the droplet.

The present inventors have established that the capsules of the invention may be prepared with a low size distribution. This is particularly advantageous, as a large number of capsules may be prepared, each with predictable physical and chemical characteristics.

The recorded size distribution of capsules prepared according to the present invention is very low. The distribution is shown, for example, in FIG. 2(b) by use of distribution bars.

As previously noted, the shell may have pores. The pores are gaps in the assembly of proteins at the shell of the capsule.

In one embodiment, the pores may be of a size to permit the passage of material therethrough. For example, components encapsulated within the capsule may pass through the pores of the shell to be released from the capsule. Conversely, the pores may be of sufficient size to allow components to pass into the shell internal space, and thereby become encapsulated. Such may be referred to as a passive diffusion encapsulation step. Such a technique may be used to provide a capsule having an encapsulant within. As described herein, the present inventors have provided alternative methods for the encapsulation of material in the shell preparation step. Such methods allow for a more efficient loading of the capsule with material, as the material is entirely encapsulated within the shell.

In one embodiment, the pores may be of a size that is too small to permit passage of material therethrough. For example, components encapsulated within the capsule may be prevented from passing through the pores of the shell, and therefore cannot be released from the capsule. Such material may be released from the capsule by, for example, disrupting the complexes that hold the shell together. Disruption of the shell in this way creates larger pores through which material may pass.

The size of a pore may be gauged experimentally using a range of encapsulated components each having a different cross-section, such as a different diameter. The cross-section may be known or may be predicted based on an understanding of the likely configuration of the component. The pore size may be determined based on which components are released from the capsule and which are not.

A capsule comprising an encapsulated component may be prepared using the methods described herein. Once the capsule (with encapsulant) is prepared, the capsule and its aqueous surroundings may be analysed for loss of material from within the shell out to the external aqueous phase. The encapsulated compounds may have an analytical label to aid detection. Suitable labels include fluorescent labels which are detectable using standard fluorescence microscopy techniques.

In one embodiment, the pore size is at most 20, at most 15, at most 10, at most 5, at most 1 or at most 0.5 μm.

In one embodiment, the pore size is at most 500, at most 300 nm, at most 200, at most 100, at most 50, or at most 20 nm.

In one embodiment, the pore size is at least 0.5, at least 1, or at least 5 nm.

In one embodiment, the pore size is in a range where the minimum and maximum pore sizes are selected from the embodiments above. For example, the pore size is in range 1 to 20 nm.

As expected, the shell pore size may be influenced by the amount of protein present in the fluid phases used during the capsule preparation. Increasing the amount of protein present (for example increasing the concentration of protein) is believed to increase the amount of crosslinking with the network, thereby reducing the size of the pores in the formed shell material.

Where an encapsulant or relatively small size is to be encapsulated, the capsule may be prepared with pores of relatively small diameter, thereby to limit or prevent loss of the encapsulant out of the shell. Where a relatively large encapsulant is to be encapsulated, the pore size may be larger.

The capsule shell may comprise one or more layers of material, where each layer is an assembly of a protein. The layers may be formed from different proteins, thereby to provide distinct layers within the capsule shell. Neighbouring layers in a capsule shell may be connected through the interaction of beta sheet structures between protein molecules in each layer.

The shell may be viewed as a mesh extending in three dimensions. Although a shell may have a depth of material, such as a thickness described herein, it is understood that the formation of the shell will nevertheless provide an internal space in which a component may reside. Thus, in one embodiment, the present invention is not intended to encompass particles having no internal space.

Alternatively the capsule shell may comprise a plurality of concentric layers of network material that are not interlinked. In any such embodiment, the reference to capsule size refers to the cross section of the outermost shell. In one embodiment, the capsule is a nested capsule where a first outer capsule holds a second inner capsules, where each capsule is a capsule having a shell of material that is an assembly of a protein, such as a fibril assembly of a protein.

In such a capsule there may be an internal space between the inside shell wall of the outer capsule and the outer shell wall of the inner capsule. This space may be suitable for holding a component, such as a component described herein. The inner capsule may itself hold a component, either instead of or in combination with the outer capsule holding a component. Where the inner and the out capsules hold a component, these components may be the same or different.

Where a component is held in the internal space between the inside shell wall of the outer capsule and the outer shell wall of the inner capsule, that component may be a hydrophobic component. Methods for the preparation of nested capsules make use of water in oil in water (for example) droplets, where the oil phase is ultimately incorporated as a fluid within the space between capsule shells formed at the droplet boundaries.

In other embodiments this internal space may simply hold a fluid, such as the oil used in the preparation methods described herein. This may be the case where the inner capsule is only very slightly smaller than the outer capsule, and there is insufficient space to hold a component between the shells of the inner and outer capsules.

As discussed above, the shell material may include detectable labels or detectable functionalities A detectable functionality is functionality of a capsule shell component having a characteristic that is detectable over and above the characteristics that are present in other components of the capsule, or even other functionalities of the same component. The detectable functionality may refer to a particular chemical group that gives rise to a unique signal in, for example, IR, UV-VIS, NMR or Raman analysis. The functionality may be a radioactive element.

Typically a part of the shell material or the encapsulant is provided with a detectable label, as the introduction of a chosen label allows the use of techniques that are most appropriate for the property that is to be measured.

The capsule shell of the invention is stable and may be stored without loss of the shell structure. The integrity of the shell therefore allows the capsule to be used as a storage vessel for an encapsulant. The capsules of the invention are thermally stable and the shell is known to maintain its integrity at least up to 100° C. The capsules of the invention are also stable at reduced pressures (i.e. below ambient pressure). The shell is known to maintain its integrity down to at least $1\times10^{-3}$ mbar (for example, as shown during the preparation of SEM images).

The capsules of the invention have a long shelf life. The present inventors have confirmed that structural integrity is maintained for at least 10 months.

The capsule of the invention may have a positive ζ-potential.

In one embodiment, the ζ-potential is at least 10, at least 15, at least 20, or at least 30 mV. The ζ-potential of a capsule may be determined using the techniques described by O'Brien et al. (*Canadian Journal of Chemistry* 59, 1878-1887 (1981) and Shimanovich et al. (*Advanced Functional Materials* 21, 3659-3666 (2011)).

The capsules of the invention do not include oligomeric forms of the protein. This is advantageous for the use of the capsules as oligomeric structures are associated with toxicity in vivo. Rather, the capsules of the invention comprise a higher order assembly of the protein that forms a shell and optionally forms a network of material within the shell.

An oligomeric form of the protein is an aggregation of the protein that is not in amyloid fibril form. In one embodiment, the oligomeric form is an assembly of 2 to 50 proteins. For example, the oligomeric form may be a dimer or trimer.

An oligomer may be regarded as a prefibrillar state of protein assembly. The oligomeric form is believed to form from monomeric peptide molecules through a fibril-catalyzed secondary nucleation reaction, rather than through a classical mechanism of homogeneous primary nucleation. See, for example, Cohen et al. PNAS 2013, 110, 9758 which discusses the formation of toxic oligomeric forms of the amyloid-β (Aβ) peptide Aβ42.

The oligomer is distinguishable from a seed, as described herein. An oligomer is generally a relatively low molecular weight assembly, which is generally limited, as noted above, to 2 to 50 proteins. In contrast, the seed is a higher molecular weight assembly that is more closely related to fibril form of the shell assembly. Seeds are described in further detail below.

Protein

The capsules of the present case are composed of an assembly of proteins. A reference to a protein is typically a reference to a naturally occurring protein, although variant and derivative forms of naturally occurring proteins are also suitable for use.

Particularly suitable for use in the present case are those proteins that are known to aggregate, for example to form fibrils. In the methods of the invention, the protein is provided in monomeric form, these monomers are permitted to self-assemble, for example under denaturing conditions. The assembly may be referred to as a fibrous protein aggregate, such as an amyloid form of the protein. The structure of the assembly is described in further detail below.

A protein may be a polypeptide having at least 10 or more amino acids, such as 20 more, 50 or more or 100 or more amino acids.

A protein for use in the present case is a protein having the ability to form an assembly, such as described herein. For example, the protein may have one or more beta sheet sequences within the secondary structure, where such structures are capable of forming cross beta sheet interactions with neighbouring proteins. Additionally, the protein may contain alpha-helix and beta-helix structures.

Proteins having the ability to self-assemble are well known in the art, and there are a large number of proteins that are known to form filamentous protein aggregates.

A protein may be a mammalian, such as a human protein, or an avian protein.

A protein for use in the present case may be selected from the groups consisting of glucagon, myoglobin, haemoglobin, bovine serum albumin (BSA), ovalbumin, silk (including native and reconstituted silk) egg yolk, immunoglobulin light chain, immunoglobulin heavy chain, β2-microglobulin, transthyretin, serum AA, apolipoprotein, such as apolipoprotein AI, AII and AIV, gelsolin, lysozyme, fibrinogen α-chain, cystatin C, ABriPP, leukocyte chemotactic factor 2, ADanPP, Aβ and Aβ protein precursor (AβPP), prion protein, calcitonin, islet amyloid polypeptide, atrial natriuretic factor, prolactin, insulin, lactadherin, kerato-epithelin, lactoferrin, odontogenic ameloblast-associated protein, semenogelin I, α-S2C and K casein, α-synuclein, polyQ expanded huntingtin, actin, neuroserpin, ferritin, tau, androgen receptor protein, ataxin-1, DRPLA, NAC, atrial natriuretic factor, betabellins 15D and 16D, cytochrome $C_{552}$, methionine aminopeptidase, phosphoglycerate kinase, egg white (lysozyme), PI3-SH3, β-lactobgolbulin, monellin, HypF, Human complement receptor, human stefin B, GAG factor, yeast prion Ure2p, herpes simplex virus glycoprotein B, adenovirus fibre, α-lactalbumin, β-lactoglobulin, and yeast protein Sup35.

Such proteins are known to form assemblies, such as aggregates. See, for example, Sipe et al. *Amyloid* 2010, 17, 101 and Uversky et al. *Biochimica et Biophysica Acta* 2004, 1698, 131.

A protein for use in the present case need not be a protein whose assembled form is associated with a disease state.

In one embodiment a protein for use in the present case may be selected from lysozyme, glucagon, insulin, myoglobin, haemoglobin, bovine serum albumin (BSA), ovalbumin, silk (including native and reconstituted silk) egg white, and egg yolk. Additionally, the proteins for use include those described by Knowles et al. *Nat. Rev. Mol. Cell. Biol.* 2014, 15, 384, which is incorporated by reference herein.

The use of lysozyme, glucagon and insulin as proteins for capsules is exemplified in the present case.

The suitability of a particular protein for forming an assembly may be determined experimentally by replacing e.g. lysozyme in the worked examples describe herein.

Where a capsule is formed having a shell that is an assembly of the protein, and that capsule is stable, then the protein is suitable for use. The presence of certain secondary structures within an assembly of a protein may be determined using standard analytical techniques. For example, FTIR analysis may be used to gauge the amount of beta sheet aggregate within an assembly. The same technique may also be used to determine the relative amount of α-helix, β-sheet (native) and random coil content.

A reference to a protein includes a reference to modified proteins, such as those having an analytical label. Where a label is provided, that label does not interfere with the protein's ability to form aggregates.

In the methods of preparation described herein, a protein is permitted to self-assemble thereby to provide a capsule shell. In these methods a reference to a protein may be a reference to that protein not in an assembly with another protein. In other embodiments, a protein may be permitted to form an assembly with another protein, where each protein may be a protein as described herein. For example, insulin and glucagon mixed assemblies, amongst others, are described herein.

In the methods of preparation a seed may be used to initiate or catalyse the formation of the capsule shell. The seed is itself an assembly of two or more proteins. Naturally, the size of the seed is smaller, and typically very much smaller, than the size of the capsule shell.

A protein may be provided in its native or functioning state, and it may be denatured during the process of preparation to allow for the formation of the assembly. The denaturing step may be required where the native state of the protein is not associated with the formation of aggregates, such as the formation of amyloid structures.

In one embodiment, a mixture of proteins may be used to form the shell and the network of material, where present. Thus, the assembly is formed from the aggregation of those proteins to form a mixed assembly.

A reference to a protein also includes a reference to a variant of that protein, such as a functional variant having the ability to self-assemble. A variant may be a polypeptide comprising an amino acid sequence having at least about 60%, at least about 70%, at least about 80%, at least about 90%, at least about 95%, at least about 98%, or at least about 99% sequence identity to a protein such as that specified above.

Variants which are polypeptides comprising an amino acid sequence at least 50% identical to a specified protein may comprise one or more amino acid additions, substitutions and/or deletions relative to the amino acid sequence of the specified protein. Variants may comprise one or several amino acid additions, substitutions and/or deletions relative to the amino acid sequence of the specified protein. Variants may comprise 1-150, 1-100, 1-50, 1-20 or 1-10 amino acid additions, substitutions and/or deletions relative to the amino acid sequence of the specified protein.

Amino acid sequence identity and similarity and nucleic acid sequence identity may be measured using standard bioinformatics software tools, such as the freely available EMBOSS, or BLAST, software tools. Default parameters are generally used. For example EMBOSS Needle pairwise sequence alignment can be used to determine amino acid sequence identity. EMBOSS Needle pairwise sequence alignment, which uses the Needleman-Wunsch algorithm (J. Mol. Biol. (48): 444-453 (1970)), can be used to determine amino acid sequence similarity, for example using default parameters and using a BLOSUM scoring matrix such as the BLOSUM62 scoring matrix. Default parameters may be used with a gap creation penalty=12 and gap extension penalty=4.

Assembly

An assembly is an aggregation of protein molecules held together by non-covalent bonding. The aggregation is formed from the self-assembly of protein molecules. The aggregation of the protein molecules may occur spontaneously under the conditions of the capsule formation step, and/or the aggregation of protein molecules may be initiated or catalysed by a seed that is provided together with the protein. As noted previously, an assembly may be an assembly of one protein or two or more different proteins.

The assembly may be regarded as a cross-linked polymer network. The cross-linking is a non-covalent interaction between polymers (i.e. proteins) within the shell of the capsule. The assembly may be fibrous protein aggregates (a fibril assembly). The structure of the assembly may be a fibril assembly having an amyloid structure.

The assembly, and therefore the capsule shell, may be insoluble, for example in water.

A protein present within an assembly is typically present in a misfolded state. The formation of the assembly may be associated with the generation of a partially folded protein during the capsule preparation. Thus, a protein in a native state may be converted to a non-native partially unfolded confirmation. In other embodiments, such as where the native protein has a native unfolded state, the formation of the assembly may include the partial folding of that protein.

A confirmation change in a protein and/or the fibrillation of a protein may be initiated by a change in the local environmental conditions. For example, a change in local pH may cause folding or unfolding, or fibrillation.

In one embodiment, the protein possesses a secondary structure within its native state. The secondary structure may be selected from beta sheet, alpha helix, beta helix and alpha sheet.

In one embodiment, the protein possess a beta sheet within its secondary structure.

Typically, the protein molecules are bound together in an assembly by interaction of beta sheet structures between neighbouring protein molecules ("cross-beta sheet"). Thus the quaternary structure includes an arrangement of proteins interacting through the beta sheet.

In one embodiment, the beta sheet structures are formed during the assembly process. In some embodiments, the formation of the assembly may be driven by beta sheet fibrillation of proteins. Other non-covalent interactions may be present within an assembly, such as electrostatic interactions and other protein interactions.

An assembly comprising fibrils may have a core cross-beta-sheet structure where continuous beta-sheets are formed with beta-strands running perpendicular to the long axis of the fibrils.

The assemblies in the present case are not limited to fibrillar forms, and other aggregate forms may be present in the capsule shell. Protein aggregation may also occur via amorphous aggregate formations, such as with proteins having a natively unfolded state. Such proteins possess little or no secondary structures and would not be expected to form aggregates based on, for example, cross beta-sheets.

In one embodiment, the assembly is an aggregation comprising fibril forms.

The assembly for use in the capsules of the present case is typically a non-covalent assembly. In certain embodiments an assembly may additionally include covalent interactions between proteins, such as dislufide bridges. Nevertheless, the non-covalent interactions are the predominant interactions for holding a protein in an assembly. The covalent interactions may form during the assembly process, under the conditions necessary to self-assemble the protein.

The assembly may include a plurality of protein fibrils that are cross-linked.

A fibril may contain two to six unbranched protofilaments. These fibrils may be from 2-5 nm in diameter. Such a fibril may associated with other fibrils, for example laterally or helically (twisted), to form larger fibrils from 4-13 nm in diameter.

The presence of the cross-beta sheet structures within the assembly may be determined through the use of dyes that are specific to cross-beta sheet structure (as described above) or by use of, for example, FTIR techniques which can be used to quantify alpha helix and beta sheet properties in an assembly.

In certain embodiments of the invention a seed is used to initiate or catalyse the formation of an assembly of the protein. The seed is itself an assembly of the protein that is pre-prepared in advance of the capsule preparation. The size of the seed is considerably smaller than the size of the final capsule.

A seed is an aggregation of the protein, and the seed may be a fibril. The seed is larger than an oligomer. The seed has a substantial fibril structure whereas the oligomer does not.

A seed for use in the methods of the invention is typically an elongate assembly of a protein having a length of, for example, from 10 to 500 nm, and a width of, for example from 1 to 10 nm.

In one embodiment, the length of a seed is at least 10, at least 50 or at least 100 nm.

In one embodiment, the length of a seed is at most 200, at most 400, at most 500 or at most 1,000 nm.

The seed used has smaller dimensions than the capsule shell it is to be used to prepare. For example, the largest dimension of the seed, such as the length, may be at most 0.5%, at most 1%, at most 5% of the diameter of the capsule (or the droplet used to form the capsule).

A seed may be regarded as an immature fibril, which is smaller in size compared to a mature fibril i.e. a fibril that is present within a formed assembly.

The preparation of a protein seed is described herein. These methods may be used to control the size of the formed seed, for example by appropriate selection of the sonication time.

The dimension of a protein seed may be determined by AFM measurements, amongst other methods.

The inventors have found that an assembly may be formed from protein optionally together with a seed. The seed alone cannot normally be used to prepare an assembly without the presence of protein monomer.

Network

In one embodiment, a capsule further comprises a network of material within the shell. The network provides an internal structure to the capsule and at least partially, such as partially, occupies the internal space defined by the capsule shell.

The network is an assembly of a protein, such as described above. The network of material is connected to and contiguous with shell. The shell and the network include the same protein. Both the shell and the network may be an assembly of a plurality of proteins.

The network may be a series of interlinked fibrils that cross the internal space of the capsule.

A network of material is typically prepared from the fluidic methods described herein where an aqueous second phase comprising the protein is dispersed in a water immiscible first phase. Here, the protein disperses throughout the dispersed region and on self-assembly an aggregation of protein is formed throughout the dispersed region, including at the boundary of the dispersed region.

A capsule without a network of material may be prepared where a water immiscible second phase is dispersed in an aqueous first phase comprising the protein. Here, the protein locates to the boundary of the dispersed region and on self-assembly, an aggregation of protein is formed at the boundary of the dispersed region.

In one embodiment a capsule does not contain a network within the shell.

Encapsulant

A capsule of the invention may be used to encapsulate a component (the encapsulant). In one embodiment there is provided a capsule comprising an encapsulant. The capsule is suitable for storing a component, and this component may be later released as required at a chosen location.

It is understood that a reference to an encapsulated component is not a reference to a solvent molecule. For example, the encapsulated component is not water or is not an oil or an organic solvent. It is also understood that a reference to an encapsulated component is not a reference to the protein for use in the preparation of the capsule shell (although the encapsulant may be a different protein, that is not involved an assembly). Otherwise, the component is not particularly limited.

The encapsulant is therefore a component of the capsule that is provided in addition to solvent that may be present within the shell and unassembled protein.

In the methods of the invention the capsule shell and optionally the internal network of material is prepared from a fluid containing protein, optionally together with a seed. Not all the protein may assemble to form the shell. Some of the protein may form a network if material, such as fibrils, that is held within the shell. This network is typically connected to the shell. Thus, the assembly of the shell and the network is continuous.

Protein and seed that is not incorporated into an assembly may also be held within the shell.

The protein and the seed may be contained within the shell, and may be contained in addition to the encapsulant. Thus, the encapsulant is a component of the capsule that is provided in addition to unassembled protein and seed that may be present within the shell.

The capsules of the invention may be used to encapsulate a wide range of components.

In one embodiment, the encapsulated component has a molecular weight of at least 100, at least 200, at least 300, at least 1,000, at least 5,000 (1 k), at least 10,000 (10 k), at least 50,000 (50 k), at least 100,000 (100 k) or at least 200,000 (200 k).

In one embodiment, the encapsulant is a therapeutic compound.

In one embodiment, the encapsulant is a biological molecule, such as a polynucleotide (for example DNA and RNA), a polypeptide (such as a protein) or a polysaccharide.

In one embodiment, the encapsulant is a polymeric molecule, including biological polymers such as those polymers mentioned above.

In one embodiment, the encapsulant is a component selected from the group consisting of virus, antibody, microorganism, and hormone.

Where the encapsulant is a protein, that protein may differ from the protein that makes up the shell of the capsule and the network of the capsule, where present.

The size of the capsule is selected so as to accommodate the size of the encapsulant. Thus, the internal diameter (the distance from innermost wall to innermost wall) is greater than the greatest dimension of the encapsulant.

In one embodiment, the encapsulant has a detectable label. The detectable label may be used to quantify and/or locate the encapsulant. The label may be used to determine the amount of encapsulant contained with the capsule.

In one embodiment, the detectable label is a luminescent label. In one embodiment, the detectable label is a fluorescent label or a phosphorescent label.

In one embodiment, the detectable label is a visible label.

In one embodiment, the fluorescent label is a rhodamine or fluorescein label.

Methods for the Preparation of Capsules

In one aspect of the invention there is provided a method for the preparation of a capsule having a shell that comprises an assembly of a protein, wherein the method comprises the step of:

(i) contacting a flow of a first phase and a flow of a second phase in a channel, thereby to generate in the channel a dispersion of discrete regions, preferably droplets, of the second phase in the first phase, wherein one of the first and second phases comprises a protein suitable for forming an assembly of proteins, thereby to form a capsule shell at the boundary of the discrete region, wherein the first and second phases are immiscible.

In the method of the invention a dispersion of the second phase is created within the continuous first phase. In one embodiment, one of the first and second phases is an aqueous phase and the other phase is a water immiscible phase.

In one embodiment, the protein is provided together with a seed for the assembly of the protein, wherein the seed is an assembly of proteins.

In one embodiment, step (i) includes heating the discrete region. The heating step may be required to form an aggregation of the protein.

The protein located at the boundary of the discrete region, and optionally dispersed within the region, may be heated to at most 80° C., at most 70° C. or at most 65° C.

The protein may be heated to at least 30° C., at least 40° C. or at least 50° C.

In one embodiment, the protein is provided in a flow that is an aqueous phase. The aqueous phase may be the first or the second phase.

In one embodiment, the first phase is an aqueous phase. In this embodiment, the capsule formed has a shell of material that is an assembly of proteins.

In one embodiment, the second phase is an aqueous phase. In this embodiment, the capsule formed has a shell of material that is an assembly of proteins and the capsule has a network of material within the shell that is an assembly of proteins.

In one embodiment, the second phase is an aqueous phase. The first phase is a water immiscible phase, for example an oil phase.

In one embodiment, the first phase is an aqueous phase. The second phase is a water immiscible phase, for example an oil phase.

In one embodiment, the second phase comprises a component for encapsulation, and the step (i) provides a capsule having a shell encapsulating the component.

In one embodiment, the method further comprises the subsequent step of (ii) heating the droplet.

In one embodiment, the method further comprises the subsequent step of (iii) collecting the outflow from the channel, thereby to obtain a droplet, which has a capsule. This step may be performed before or after the heating step.

In one embodiment, the flow of the second phase is brought into contact with the flow of the first phase substantially perpendicular to the first phase. In this embodiment, the channel structure may be a T-junction geometry. The path of the channel may follow the path of the flow of the first phase, in which case the second flow will be substantially perpendicular to the resulting combined flow in the channel. Alternatively, the path of the channel may follow the path of the flow of the second phase, in which case the first phase flow will be substantially perpendicular to the resulting combined flow in the channel.

Methods utilising a T-junction geometry provide discrete regions, typically droplets, of the aqueous phase in the oil phase as a result of induced shear forces within the two phase system.

In one embodiment, an additional flow of the first phase is provided. The first phase flows are brought into contact with each side of the second phase flow in a channel, and the flow of phases is then passed through a region of the channel of reduced cross-section (an orifice) thereby to generate a discrete region, preferably a droplet, of the second phase in the channel. Such methods, which have an inner second phase flow and two outer first phase flows, are referred to as flow-focusing configurations.

Methods using flow-focusing techniques provide discrete regions, typically droplets, of the second phase in the first phase as a result of the outer first phase applying pressure and viscous stresses to the inner second phase, thereby generating a narrow flow of that phase. This narrowed flow then separates into discrete regions, typically droplets, at the orifice or soon after the combined flow has passed through the orifice.

In one embodiment, the discrete region is a droplet.

In one embodiment, the discrete region is a slug.

After the discrete region is formed in the channel, the discrete region may be passed along the channel to a collection area. The residence time of the discrete region in the channel is not particularly limited. In one embodiment, the residency time is sufficient to allow the shell to form.

As the discrete region is passed along the channel it may be subjected to a mixing stage whereby the components of the discrete region are more evenly distributed around that discrete region. In one embodiment, the channel comprises a winding region. The winding region may take the form of a substantially sigmoid path through which the discrete region is passed.

In one embodiment, the second phase further comprises a component for encapsulation, and the step (i) provides a capsule encapsulating the component.

Discrete regions of second phase are generated in the channel as the immiscible first phase shears off the second phase. The frequency of shearing is dependent on the flow rate ratio of the two phases.

In one embodiment, the flow rate is selected so as to provide a set number of droplets per unit time (droplets per second).

The droplets may be prepared at a rate of at most 10,000, at most, 5,000, at most 1,000 or at most 500 Hz.

The droplets may be prepared at a rate of at least 1, at least 10, at least 50, at least 100, or at least 200 Hz.

In one embodiment, the droplets may be prepared at a rate that is in a range where the minimum and maximum rates are selected from the embodiments above. For example, the rate is in range 100 to 500 Hz.

In one embodiment, the method comprises the step of (iii) drying the capsule. The drying step at least partially removes solvent (which may be water or organic solvent) from the capsule and may be referred to as desolvation.

There are no particular limitations placed on the method for drying the capsules. In one embodiment, the capsules obtained may simply be allowed to stand at ambient conditions, and the solvent permitted to evaporate.

In one embodiment, the method optionally comprises a washing step, whereby the capsules obtained are washed with a solvent. The purpose of the washing step may be to remove surfactant (where used) or any other component used in the shell-forming step.

In one embodiment, the method comprises the drying the capsule and subsequently resolvating the capsule. The resolvation step may be performed minutes, hours, days, weeks or months after step (iii) is complete.

In one embodiment, a reference to a size of a droplet is also a direct reference to a size of a capsule. The droplet is a droplet formed in a channel of a fluidic device or a droplet that is collected from the channel of such a device. The size refers to a droplet that has not been subjected to a drying step.

A capsule formed directly after preparation is substantially spherical. Desolvation of the capsule may result in the collapse of the capsule as the spherical edge becomes distorted. The shell material appears to fold in a random manner.

In the preparation method described herein, a droplet is formed and the shell of a capsule forms at the interface of the droplet. The formed droplet may be subjected to a desolvation step, thereby resulting in the shrinkage of the capsule shell. In one embodiment, the size of the capsule refers to the size of a capsule that has been subjected to a dehydration step.

The flow rate of the first phase and/or the second phase may be varied to allow preparation of droplets, and therefore capsules, of a desired size. As the flow rate of the first phase is increased relative to the second phase, the average size of the droplet decreases, and the formed capsule size decreases also.

Typically, the flow rate of the first phase is at least 1.5, 2, 3, 4, 5 or 10 times greater than that of the second phase.

In one embodiment, the flow rates of the first and the second phases are selected so as to provide droplets having a desired average diameter.

The average particle size may be determined from measurements of a sample of droplets collected from the flow channel using simple microscopy techniques.

In one embodiment, the each droplet is a microdroplet.

In one embodiment, the each droplet is a nanodroplet.

In one embodiment, the average size of the droplet is at least 0.1, 0.5, 0.6, 1, 5, 10, 20, 30, or 40 µm in diameter.

In one embodiment, the average size of the droplet at most 1,000, 600, 400, 200, 100, 75 or 50 µm in diameter.

In one embodiment, the average size of the droplet is in a range where the minimum and maximum rates are selected from the embodiments above. For example, the average size is in the range 0.6 to 600 µm.

The droplet formed from the fluidic preparation has a narrow size distribution. This may be gauged empirically by observation of the packing of collected droplets. A hexagonal close packing arrangement of collected droplets is indicative of a low monodipsersity value (see, for example, L. J. De Cock et al. *Angew. Chem. Int. Ed.* 2010, 49, 6954).

In one embodiment, the droplets have a relative standard deviation (RSD) of at most 1.5%, at most 2%, at most 4%, at most 5%, at most 7%, or at most 10%.

The concentration of the protein as used in the first phase or second phase may be altered. Changes in concentration of the protein may alter the physical and chemical properties of the shell material subsequently formed, and the nature of the network of material within the shell, if present.

In one embodiment, the concentration of protein may be altered in order to increase the thickness of the shell and/or to decrease the number and/or size of pores in the capsule shell. An increase in the concentration of protein may be associated with an increase in the extent of the network of material within the shell.

In one embodiment, the concentration of the protein in the first or second phase is at least 0.05, at least 0.1, at least 0.2, at least 0.3, at least 0.5, at least 1.0, at least 5.0 or at least 10 µM.

In one embodiment, the concentration of the protein in the first or second phase is at most 500, at most 200, at most 100, at most 75, at most 50 µM.

In one embodiment, the concentration of the protein in the first or second phase is in a range where the minimum and maximum rates are selected from the embodiments above. For example, the concentration of the concentration of the protein in the first or second phase is in the range 1 to 50 µM.

Alternatively, the protein concentration may be expressed by weight %. Thus, in one embodiment, the concentration of the protein in the first or second phase is at least 0.1, at least 0.5, at least 1.0 or at least 2.0 wt %.

In one embodiment, the concentration of the protein in the first or second phase is at most 10, at most 15, or at most 20 wt %.

In one embodiment, the concentration of the protein in the first or second phase is in a range where the minimum and maximum rates are selected from the embodiments above. For example, the concentration of the concentration of the protein in the first or second phase is in the range 1.0 to 10 wt %.

In one embodiment, a seed is provided together with the protein.

In one embodiment, the seed is provided at provided at a concentration that is less than the concentration of the (monomeric) protein. The seed may be present in the first or second phase at 40, 30, 25, 20, 10, 5, 2, 1 or 0.5 mole % or less with respect to the mole concentration of the protein in the first or second phase.

In one embodiment, the concentration of the seed in the first or second phase is at most 1, at most 0.5, at most 0.2 µM.

In one embodiment, the concentration of the seed in the first or second phase is at least 0.01, at least 0.02, at least 0.05, at least 0.1 µM.

Alternatively, the seed concentration may be expressed by weight %. Thus, in one embodiment, the concentration of the seed in the first or second phase is at least 0.01, at least 0.05, at least 0.1, at least 0.5, at least 1.0 wt %.

In one embodiment, the concentration of the seed in the first or second phase is at most 5 or at most 10 wt %.

In one embodiment, the concentration of the seed in the first or second phase is in a range where the minimum and maximum rates are selected from the embodiments above. For example, the concentration of the concentration of the seed in the first or second phase is in the range 0.1 to 5 wt %.

In one embodiment, the discrete region is formed at ambient temperature.

In one embodiment, the discrete region is formed at about 5, 10, 15, 20, 25, or greater than 25° C. As noted above, the discrete region, once formed, may subsequently be heated as part of the procedure for forming an assembly of the protein.

Apparatus

The methods of the present invention call for a flow of a second phase and a flow of a first phase, which is immiscible with the second phase, to be brought together in a channel, thereby to generate a dispersion of the second phase in the first phase. Methods for the generation of a flow of a first phase and a second phase are well known in the art. In one embodiment, each flow may be generated from a syringe under the control a programmable syringe pump. Each syringe is loaded with an appropriate aqueous solution or water-immiscible phase.

In the method of the invention, droplets may be collected only when the flows are at the required flow rate.

The channel in which the second phase and first phase flows are contacted is not particularly limited.

In one embodiment, the channel is a microfluidic channel.

In one embodiment, the channel has a largest cross-section of at most 1,000, at most 500, at most 200, at most 100 or at most 50 µm.

In one embodiment, the channel has a largest cross-section of at least 0.1, at least 1, at least 10 or at least 20 µm.

The channel may be provided in an appropriate substrate. The substrate is one that will not react with the components of the complexable composition.

The substrate may be a PDMS-based substrate.

The preparation of substrates for use in fluidic flow techniques are well known to those of skill in the art. Examples in the art include the preparation described by Yang et al. (Yang et al. *Lab Chip* 2009, 9, 961), which is incorporated herein.

Second Phase

The second phase is immiscible with the first phase. The second phase may be referred to as a dispersed phase, particularly once it has contacted the first phase and is separated into discrete regions, such as droplets.

In one embodiment, one of the first or second phases is an aqueous phase. Therefore, the other of the first or second phases is water immiscible.

Typically the protein is provided in an aqueous phase. This may be the first or second phase. When the protein is provided in the second phase, a capsule may be formed having a shell that is an assembly of protein and the capsule is optionally provided with a network of material within the shell that is an assembly of proteins. When the protein is provided in the first phase, a capsule may be formed having a shell that is an assembly of protein. Here, the capsule does not have a network of material within the shell that is an assembly of proteins.

In one embodiment, the flow rate of the second phase is at most 1,000, at most 500, at most 250, or at most 100 µL/min.

In one embodiment, the flow rate of the second phase is at least 0.05, at least 0.1, at least 0.5, at least 1, at least 5, at least 10, or at least 50 µL/min.

In one embodiment, the flow rate of the second phase is in a range where the minimum and maximum rates are selected from the embodiments above. For example, the flow rate of the second phase in the range 0.1 to 100 µL/min.

The flow rate of the second phase refers to the flow rate of that phase before the phase is contacted with the first phase.

First Phase

The first phase comprises a component that is immiscible with the second phase. The first phase may be referred to as a continuous or carrier phase.

In one embodiment, the flow rate of the first phase is at most 1,000, at most 500, or at most 250 µL/min.

In one embodiment, the flow rate of the first phase is at least 10, at least 50, or at least 100 µL/min.

In one embodiment, the flow rate of the first phase is in a range where the minimum and maximum rates are selected from the embodiments above. For example, the flow rate of the first phase in the range 100 to 250 µL/min.

The flow rate of the first phase refers to the flow rate of that phase before the phase is contacted with the second phase.

Where a flow focusing technique is used to develop discrete regions of a second phase, the flow rates of the two first phases may be the same.

The first phase may additionally comprise a surfactant. The surfactant is provided in the first phase in order to stabilise the macroemulsion that is formed in the fluidic preparation methods. The step of forming the discrete region (such as a droplet) may require the presence of a surfactant. Furthermore, the presence of a surfactant is useful in limiting or preventing the coalescence of the droplets collected.

The surfactant chosen is not particularly limited, and encompasses any surfactant that is capable of promoting and/or stabilising the formation of discrete regions, such as droplets, of the second phase in the first phase.

Suitable surfactants for use in the present invention include those described by Holtze et al. *Lab Chip* 2008, 8, 1632. Typically such surfactants comprise an oligomeric perfluorinated polyether (PFPE) linked to a polyethyleneglycol. Such surfactants are especially useful for stabilising water-in-fluorocarbon oil emulsions.

The surfactant is present at most 0.1%, at most 0.2%, at most 0.5%, at most 0.75%, at most 1%, at most 2%, at most 5% w/w to the total phase.

The surfactant is present at least 0.05% or at least 0.07% w/w to the total phase.

Where the first phase is an aqueous phase, the surfactant may be polyvinyl alcohol.

In one embodiment, the first phase has a solubility in the second phase of at most 50, at most 20, at most 10, or at most 5 ppmw.

In one embodiment, second phase has a solubility in the first phase of at most 50, at most 20, at most 10, or at most 5 ppmw.

Aqueous Phase

The present invention calls for the use of an aqueous phase either as the continuous or dispersed phase in the methods of the invention. Methods for the preparation of suitable aqueous solutions comprising the protein will be apparent to those of skill in the art.

The aqueous phase may include agents to denature the protein, for example to aid the formation of an assembly of the protein.

The aqueous phase may be acidic, alkaline or neutral, preferably acidic or alkali. The aqueous phase may include salts, polymers including biological polymers such as dextran and other polysaccharides, seeds such as described above, particles such as nanoparticles (for example magnetic nanoparticles).

Water Immiscible Phase

The present invention calls for the use of a phase that is immiscible with water. That phase may be an oil-based phase (oil phase) or an organic solvent-based phase (organic phase), or a combination of the two.

In one embodiment, the water immiscible phase is a liquid phase.

The oil phase has as a principal component an oil. The oil is a liquid at ambient temperature.

The oil is inert. That is, it does not react with the protein, or any other component used to form a capsule of the invention. The oil does not react with the shell.

In one embodiment, the oil is a hydrocarbon-based oil.

In one embodiment, the oil is a mineral oil.

In one embodiment, the oil is a fluorinated hydrocarbon oil.

In one embodiment, the oil is a perfluorinated oil. An example of a perfluorinated for use in the invention is FC-40 (Fluoroinert as available from 3M).

In one embodiment, the oil is a silicone oil.

In one embodiment, the water immiscible phase has as a principal component an organic solvent. For example, the organic solvent is selected from chloroform and octane.

Capsule with Encapsulant

The methods of the invention are suitable for the incorporation of a component into a capsule. The capsule produced therefore comprises an encapsulated material (an encapsulant).

In a further aspect of the invention there is provided a method for the preparation of a capsule having a shell that comprises an assembly of proteins, wherein the method comprises the step of:

(i) contacting a flow of a first phase and a flow of a second phase in a channel, thereby to generate in the channel a dispersion of discrete regions, preferably droplets, of the second phase in the first phase, wherein one of the first and second phases comprises a protein suitable for forming an assembly of proteins, and the second phase comprises a component for encapsulation, thereby to form a capsule shell at the boundary of the discrete region, wherein the capsule holds the component and the first and second phases are immiscible.

The method of the invention is particularly attractive as it allows all the component present in the second phase flow to be encapsulated within the capsule shell. The formation of the capsule shell occurs at the boundary of the droplet at the interface with the first phase. Substantially all the component, therefore, is encapsulated within the formed shell. The present method therefore provides an efficient method for the incorporation of component into a capsule.

In one embodiment, the method is a method for the preparation of a capsule encapsulating a plurality of components. In this embodiment, the aqueous phase comprises at least a first component to be encapsulated and a second component to be encapsulated. The plurality of components may be provided in separate sub-flows that are contacted prior to contact with the first phase or at substantially the same time as the second phases are brought into contact with the flow of the first phase In one embodiment, the concentration of a component to be encapsulated in the second phase is at least 0.01, at least 0.02, at least 0.05, at least 0.1, at least 0.2, at least 0.3, at least 0.5, at least 1.0, or at least 5.0 µM.

In one embodiment, the concentration of a component to be encapsulated in the second phase is at most 5,000, at most 1,000, at most 500, at most 200, at most 100, at most 75, at most 50, or at most 10 µM.

In one embodiment, the concentration of a component to be encapsulated in the second phase is in a range where the minimum and maximum rates are selected from the embodiments above. For example, the concentration of a component to be encapsulated in the second phase is in the range 0.01 to 5 mM, such as 0.02 to 50 µM.

In one embodiment, the concentration of the component to be encapsulated refers to the concentration in the second phase after any sub-flows, where present, have been brought together.

The concentration of the component in the second phase may also represent the concentration of the component held within the capsule.

The present invention provides a capsule that is obtained or obtainable from any of the methods described herein. The capsule may comprise an encapsulated component, which may also be prepared using the methods described herein.

Analysis of Capsule

In the sections above, the analysis of the shell material, shell shape, shell dimensions is described. For example, the capsule may be analysed by simple bright field microscopy to determine the shape of the capsule shell. The images obtained may also be used to determine the cross-section, typically the diameter, of the capsule shell.

The capsule shell may also be analysed for shape, cross-section and its thickness using scanning electron microscopy and confocal microscopy.

The present inventors have usefully incorporated a detectable label into the shell material (i.e. by using labelled protein), thereby to allow each to be located and defined. Where that label is a fluorescent label, it may be detected by laser scanning fluorescent microscopy, for example.

Method of Modifying a Capsule

In a fourth aspect of the invention there is provided a method for modifying a capsule of the first aspect of the invention, the method comprising the steps of:
  (i) providing a capsule having a shell of material that is a non-covalent self-assembly of a protein as described herein, wherein the capsule optionally comprises a network of material within the shell, which network is a self-assembly of the protein;
  (ii) contacting the capsule with a protein, such as a non-assembled protein;
  (iii) permitting the protein to participate with the assembly of proteins at the shell and/or optionally to participate in the assembly of proteins in the network of material, where present.

The inventors have found that a capsule of the invention, such as prepared by the methods described herein, may subsequently be modified by contacting the capsule with a protein that is able to participate in the assembly of a protein. Typically the capsule is contacted with a protein, such as monomeric protein, and which is the same as a protein that is present in an assembly, either within the shell or with the internal network, where such is present.

The method may be used to tune the properties of the capsule after the initial capsule preparation step, for example to increase the density of protein within the capsule, which may be useful in providing additional structural integrity to the capsule and/or may decrease the number and size of pores, which in turn may improve the ability of the capsule to retain encapsulated material.

The method for modifying a capsule is shown schematically in FIG. 4 (*e*).

Use of Capsules

The capsules described herein are suitable for use as encapsulants for material. This material may be stored within the capsule and released from the capsule as required. In one embodiment there is provided a capsule of the invention comprising an encapsulated component.

In a further aspect there is provided a method of delivering a component to a location, the method comprising the steps of:
  (i) providing a capsule having a shell encapsulating a component, as described herein, wherein the capsule optionally comprises a network of material within the shell, which network is a self-assembly of the protein;
  (ii) delivering the capsule to a target location;
  (iii) releasing the component from the shell.

In other aspects of the invention the capsule of the invention may be used to deliver the protein that makes up the shell and the network, where present, to a target location. As shown in the worked examples, the self-assembly of a protein may be disrupted, thereby leading to the dispersion of protein from the self-assembly. In this way, the material making up the capsule may be released.

Thus, in a further aspect of the invention there is provided a method of delivering a protein to a target location, the method comprising the steps of:
  (i) providing a capsule having a shell of material that comprises a self-assembly of a protein, as described herein, wherein the capsule optionally comprises a network of material within the shell, which network is a self-assembly of the protein;
  (ii) delivering the capsule a target location;
  (iii) disrupting the shell of material that is a self-assembly of a protein, thereby to release the protein.

In one embodiment, a location is in vivo.

In one embodiment, a location is ex vivo.

In one embodiment the release of an encapsulated component or a protein is in response to an external stimulus.

In one embodiment the release of the encapsulated component a protein is in response to a change in the local conditions.

In one embodiment, the change in local conditions may be a change in pH, a change in temperature, a change in oxidation level, change in concentration, or the appearance of a reactive chemical entity.

In one embodiment, the capsule may be disrupted in response to the dilution of the capsule. For example, a capsule may be diluted 10 fold or more, 100 fold or more, or 1,000 fold or more.

The diluent is typically aqueous diluent, such as water.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL

Protein Capsules and Particles

Single-shell capsules based on lysozyme were prepared as described below in initial proof of concept experiments. Following this, further single-shell capsules were prepared and these were compared with multishell capsule (See Multishell Capsules below).

Materials

Hen egg white lysozyme, fluorinert FC-70 (Sigma), Thioflavin T (ThT), Remazol Brilliant BlueR (RBBR), Tetracycline (Tet) and Pinicillin V were purchased from Sigma-Aldrich. The surfactant N,N-bis-(n-propyl) polyethylene oxide-bis-(2-trifluoromethyl polyperfluoroethylene oxide) amide was synthesized as described by Holtze et al.

Seed Formation

A seed for use in the formation of a capsule having an assembly of a protein may be prepared using an adaptation of the method described below, which describes the formation of a lysozyme seed.

1) Dissolve 120 mg of lysozyme in 1 mL buffer solution (Buffer: 200 μL of 1M HCL, 200 μL of 2M NaCl, 600 μL of 10 mM HCL);
2) Heat lysozyme solution for 22-24 h at 65° C., whilst stirring;
3) After 22-24 hours, sonicate the solution using sonication probe (amplitude 45-50%) for 5 cycles each of 1 min;
4) Heat lysozyme solution for additional 22-24 h at 65° C., whilst stirring; and
5) Sonicate the solution using sonication probe (amplitude 45-50%) for 5 cycles each of 1 min.

Figure 13:
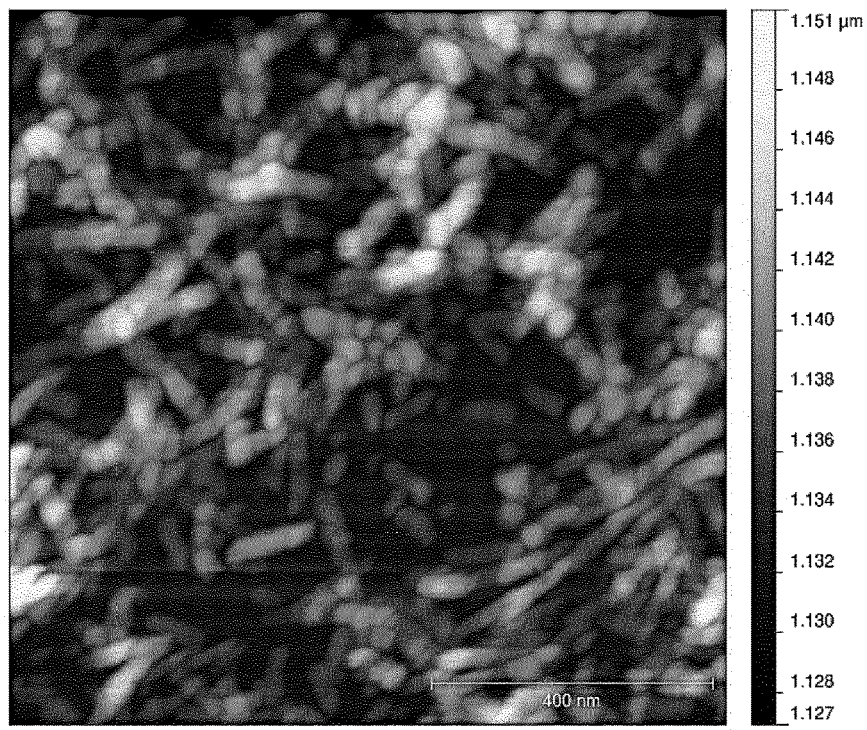
FIG. 13 is an AFM image of a lysozyme seeds formed by the Seed Formation method described herein. The scale bar is 400 nm.

The seeds were analyzed by AFM. Thus a 1 mM seed solution was prepared and a 20 μL drop of the solution was placed on a mica slide, dried at room temperature for 1 h, then analyzed by AFM. An example AFM image is shown in FIG. 13.

Droplet Microfluidics

The microfluidic droplet maker was fabricated in polydimethylsiloxane (PDMS) using soft lithography techniques (Qin et al.). Microdroplets were generated by flow-focusing (Anna et al.) from an aqueous solution of 6% (w/w) lysozyme in 20 mM HCL and 19.5 mM NaCl and 1.9 ppm (w/v) NaN$_3$ and a continuous outer phase of FC40 (Sigma) fluorinated oil containing 2% w/v of N,N'-bis-(n-propyl) polyethylene oxide-bis(2-trifluoromethyl polyperfluoroethylene oxide) amide surfactant.

Typically, the aqueous phase contained 2% w/w preformed aggregates (seeds) to accelerate the conversion of protein monomers into fibrillar form (except for the studies shown in FIG. 3 where the concentration was varied as indicated in the caption).

The aqueous flow rates used in the microfluidic device were typically in the range 20 μL/h to 1,000 μL/h. The non-aqueous flow rates (typically an oil phase) used in the microfluidic device were typically in the range 20 μL/h to 2,000 μL/h.

Capsule Formation

Capsules were prepared by forming microdroplets of a concentrated aqueous solution of the precursor polymer (Langer et al. *Nature* 428, 487-492 (2004)), here the abundant protein lysozyme (Booth et al. *Nature* 385, 787 (1997)), in an immiscible oil phase as a microemulsion created in the microfluidic droplet maker. The conversion of the soluble protein into an amyloid gel (Dobson *Nature* 426, 884-890 (2003)) was then initiated through incubation of the microemulsion at 65° C. A schematic representation of the capsule formation is shown in FIG. 1a, where the capsule produced has a shell of material that is an assembly of proteins (the lysozyme), and the capsule is provided with a network of material within the shell that is an assembly of proteins (also lysozyme).

This general synthetic approach (FIG. 1 (b)) can be expanded to generate hollow gel shells (FIG. 1 (d)). To this effect, the aqueous and oil phases were inverted, while otherwise keeping the fabrication protocol identical. The capsule formed has a shell of material that is an assembly of proteins (the lysozyme). In this synthesis the capsule preparation does not result in the formation of a network of material within the shell that is an assembly of proteins.

The resulting capsules were visualised using Nile red (Feng et al. *Bioresour. Technol.* 128, 107-112 (2013)) staining of the proteinaceous content followed by examination using confocal microscopy (FIGS. 1 (c) and (f)). A difference in the spatial localisation of the fluorescence signal was observed between the capsules produced from oil-in-water micro-droplets compared to the water-in-oil strategy. Whereas the fluorescence is emitted throughout the volume of the particles in the latter case (FIG. 1 (c)), only a fluorescent outer shell was observed in the former case (FIG. 1 (f)).

This observation, which was confirmed by a complete reconstruction of the particles using z-stacked images (FIGS. 1 (c) and (f)), suggests that the protein localises on the interface between the aqueous and oil phases when the droplets are synthesised as an oil-in-water emulsion and the assembly that is formed during incubation takes the form of a hollow capsule shell in the latter case, whereas in the former case an internal network of material is present.

After the microdroplets were formed, they were incubated for 24 h at 65° C. in order to promote gelation. In order to separate the capsules from the continuous oil phase and from the protein molecules which were not incorporated into the capsule shell or network, 500 μL of 10 mM HCl was added to a 1 mL of capsule suspension in FC40, mixed, and then centrifuged at 700 rpm for 1 minute. The emulsion phase at the oil-water interface was collected and this washing procedure repeated 3 times.

Control over the size of the capsules was achieved by regulating the channel width of the microfluidic droplet maker and the relative flow rates of the oil and aqueous phases. In this manner, the size of the capsules could be tuned to over two orders of magnitude, from more than 60 μm down to 600 nm (see FIG. 2).

Interestingly, the ζ-potential, a measure for the electric potential of the interfacial layer based on the electrophoretic mobility of the capsules (O'Brien et al. *Canadian Journal of Chemistry* 59, 1878-1887 (1981)), systematically decreased with the size, in agreement with observations of other forms of protein capsules (Shimanovich et al. *Advanced Functional Materials* 21, 3659-3666 (2011)). The ζ-potential was in all cases positive, as expected for particles formed from a positively charged protein (lysozyme). The absolute values, however, ranged from 46 mV to 8 mV, therefore spanning the range from stable to unstable colloidal suspensions.

It is noted that the capsules described by Shimanovich et al. are sonically formed capsules where the proteins are cross-linked by disulphide bonds, or through the use of cross-linking agents.

A range of different morphologies of capsules was generated by varying the ratio of free soluble lysozyme to seed (pre-formed seed fibrils) in the reaction fluids prior to dispersion. The resulting capsules were studied at high resolution using scanning electron microscopy and confocal microscopy (see FIG. 3). SEM revealed that the surfaces of the capsules (the capsule shell) became, on average, rougher with increasing seed concentrations. An increase in the initial concentration of the monomeric lysozyme, by contrast, has only a small effect on the morphology. In order to confirm that the increase in surface roughness stems from an increase in the proportion of fibrillar content of the particles, the internal structure of the particles was imaged with confocal fluorescence microscopy (see below), making use of the enhanced and red-shifted fluorescence of Thioflavin-T (ThT) upon binding to amyloid fibrils (Hsu et al. *J. Phys. Chem. B* 2013, 4, 3459). FIG. 3 (*b*) demonstrates that the fluorescence signal stemming from amyloid-bound ThT increases systematically with increasing seed concentration.

In the case of the highest added seed concentrations, the added mass amounts to less than 7% of the total lysozyme concentration in the particles and the gelation is driven entirely by the growth of these seed structures rather than by cross-linking of the seeds themselves.

The images of the particles formed with the highest concentration of seeds (FIG. 3 (*a*)) indicate that the soluble protein has almost quantitatively been transformed into fibrils. An increase in the concentration of soluble protein, by contrast, does not lead to a systematic increase in fibrillar content for a fixed incubation time of 24 h at 65° C.

Therefore, the internal structure and morphology of the capsules can be controlled by varying the absolute and relative concentrations of soluble lysozyme and/or seed fibrils in the aqueous phase used to form the droplets as well as the incubation time at elevated temperature.

The capsules were found to be able to release their component protein molecules over time when transferred from their growth environment at pH 2.0 to physiological conditions. Studies of the release of the protein molecules were conducted by measuring the increase in UV absorption in the soluble phase which corresponds to the increased presence of soluble protein after its release from the gel particles. The data reveal that this release takes place in two phases: a fast phase over a time scale of less than an hour, which releases 30-50% of the protein, and a slow phase, which occurs over days to weeks, and which results in the complete dissolution of the capsules.

The ratio of the fast to the slow phase can be controlled by tuning the density of the gel network and the fraction of free to fibrillar proteins. For capsules that contained a large fraction of free protein, the fast phase had a larger amplitude, suggesting soluble protein molecules trapped in the pores of the microgel are released. By contrast, slow phase can be attributed to the dissociation of molecules from the nanofibrils composing the gel. It is well established from other studies that the rate of dissolution of amyloid fibrils can take place over time scales of hour to days.

The capacity of the capsules to act as carriers for small molecules was investigated. The ability of lysozyme capsules to encapsulate drugs, as well as their loading capacity, was studied under physiological conditions for four types of drug-like molecules: ThT, RBBR, tetracycline (tet) and penicillin V, resulting in representative distribution in hydrophilicity and affinity to proteins.

For these encapsulation studies the precursor drug molecules were mixed with aqueous solutions of lysozyme. The conditions used were: (1) ThT dissolved in doubly distilled acidified water (pH=2), at a concentration of $6.58 \times 10^{-5}$ M; 2); RBBR was dissolved in acidified water (pH=4) at a concentration of $7.31 \times 10^{-5}$ M; 3); penicillin V $9.4 \times 10^{-4}$ M (acidified water pH=2); and 4) tetracycline was dissolved in water (pH=5) at an initial concentration of $9 \times 10^{-4}$ M. The preparation of capsules holding a drug is shown schematically in FIG. 4 (*a*), where a drug is contained in the dispersed phase (the aqueous phase in the schematic).

The loading efficiency of the drug molecules into the lysozyme capsules was studied by following the changes in UV and fluorescent spectra of the drug. The loading efficiency studies for all the four types of drug molecules are summarised in FIG. 4 (*c*). For all encapsulated species a loading efficiency in access of 80% was achieved for the successful incorporation of the small molecules into the capsules.

The release of the encapsulated species from the capsules was then studied. To this effect, the capsules were incubated in fresh buffer for an increasing period of time, removed the gels by centrifugation, and measured the concentration of released small molecules in the supernatant through their UV absorption. The results shown in in FIG. 4 (*d*) reveal marked differences in the rate of release of the small molecules.

ThT exhibited the strongest affinity for the protein microgel and was not fully released even after one week, a results originating from the expected strong interaction of ThT with amyloid fibrils. In contrast, Penicillin V reached its maximum release rate after one hour. Behaviour similar to Penicillin V was observed for RBBR and tetracycline.

The release kinetics were then studied in a cell culture medium designed to mimic in vivo conditions. Here, the lysozyme capsules were found to be stable and the release kinetics were not affected by the biological medium, α-MEM. The effect of pH on the kinetics was probed for the pH values varying from 1 to 12. The rate of the release of the four compounds from the capsules remained constant for low pH but was observed to change significantly when the pH reached value of 8.5. At pH 9, the rate of the release increased by 6% for the four molecules as a result of the onset of the gradual dissociation of the fibrils that are present in the capsule. At higher pH value 12 the degradation of the capsules was very rapid and was accompanied by the rapid release of the encapsulated cargo molecules.

The mechanism of release of small molecules from the capsules was studied by following the morphological changes of the capsules by SEM as well as through the appearance of protein in the soluble phase. The results reveal that the release mechanism of the encapsulated drug molecules from the lysozyme capsule follows a multistep process. In a first stage, unbound small molecules in the vicinity of the interface are released into solution; a second slowed timescale for release coincides with the dissolution of the capsules leading to the liberation of the remaining components.

A particular feature of the capsules of the invention is that an assembly, whether present in the shell or the network held within the shell, may be tuned by exposing that assembly to monomeric precursor proteins. For example, the density of the fibril network held within the shell may be altered, such as increased. This is shown schematically in FIG. 4 (*e*), where the incubation of a capsule within a solution that contains monomeric lysozyme results in the sequestration of the monomers within the capsule, leading to the growth of the component fibrils within, with an associated increase in the density of the network within the capsule. Thus, unlike conventional gels based on synthetic polymers, the amyloid capsules may undergo self-assembly processes to increase the density of the filament network in their core even after they have formed leading to a tuneable dynamic material.

Whether or not the increased local concentration of small molecule drugs achieved through encapsulation could lead to more effective pharmacological action was considered. The antibacterial activities for the released tetracycline and Penicillin V were probed using *Staph. a.* bacteria strains and compared with the antibacterial activity exhibited by the antibiotics at the same concentration in free solution in the absence of capsules (see below).

For both antibiotics, the loaded lysozyme capsules (FIG. 5 (*b*)) showed significantly enhanced antibacterial activity: 20% and 60% enhancement for low and high capsule concentrations.

In order to establish the biocompatibility of the lysozyme capsules, a toxicity assay was performed using human cancer U2OS cells (see also below). The MTT25 assay was performed to evaluate the viability of the cells after exposure to the capsules and a suspension containing released species from lysozyme capsules. The assay was also used to test the activity of a precursor mixture of protein, seed and drug prior to formation of the lysozyme capsule.

The results shown in FIG. 5 (*a*) demonstrate that all types of solutions were found to be non-toxic to the human cell lines which suggests that lysozyme capsules are biocompatible, and suitable for use as a drug delivery agent. The use of preformed seed fibrils to initiate the amyloid aggregation leading to gelation allows the potentially toxic oligomeric structures in protein aggregation to be avoided.

Confocal Microscopy

For confocal fluorescent microscopy, samples were prepared by depositing the aqueous dispersions, without further purification, onto glass slides. The protein microgels were analysed using a confocal microscope (Laser Scan Confocal, Zeiss Microscope) with the following lasers: UV 405 nm at 25 mW (for violet excitation) and tenable Argon 458/477/488/514 nm at 30 mW (for green excitation). The 3D images were reconstructed using the Imaris image analysis software (on average 235 z-stack slices per each protein shell).

Scanning Electron Microscopy

In order to keep the spherical shape of the protein gels intact, the capsules were deposited onto rounded cover slip glass slides and dried under low vacuum conditions in a chamber with a pressure of $1 \times 10^{-3}$ mbar, pumping rate $1 \times 10^{-5}$ mbar L/s at 25° C. After drying, a 20 nm gold layer was deposited using a vacuum sputtering coater (Denton Vacuum Desk IV) and the sample was imaged with a JEOL JSM-840 SEM.

Efficiency, Loading Capacity and Release Kinetics Measurements

The loaded microgels were washed with 10 mM HCl at intervals of time from 10 min to 14 d. The solutes after each washing were analysed by UV spectroscopy.

Antibacterial Assays

The activity of the two types of antibiotics tetracycline and penicillin V was probed and inhibition zones were compared with three sets of diluted solutions of the free antibiotics. The drops of solution were positioned on agar plates containing bacterial strains (O.D. 0.3), and inhibition zones were measured after 28 hours.

Toxicity Assays

A sample of U20S cells (2 mL) was incubated in low glucose DMEM media (Cole et al. *Cancer Chemother. Pharmacol.* 1986, 17, 259) with 0.5 mL of following solutions for 48 h at 37° C.: 1) the precursor solution of lysozyme monomers and lysozyme seeds; 2) lysozyme capsules (microgels); 3) washing solution of lysozyme gels; 4) lysozyme gels loaded with tetracycline; 5) washing solution of tetracycline loaded lysozyme microgels. The incubation medium was first removed, then cells were transferred into smaller volume plates and the media was exchanged with 80 μl of fresh solution. A 20 μL portion of MTT was then added (5 mg/mL stock solution) and the cells were incubated at 37° C. for 3 h. The medium was removed, and then 150 μL of DMSO was added and the system allowed to incubate for 10 min. The solutions were then mixed by pipetting, and the absorbance of each well at 490 nm was measured.

Capsule Dissociation

The morphological changes (using SEM and TEM) of the capsules were studied as a function of washing time in deionised water. It was observed that protein molecules first detached from the outer surface of the capsule (FIG. 6). Then, pores were detected on the surface of the capsules, which grew in size as a function of size up to 300 nm size after 12 h. The morphology of the released species also changed with increase in washing time. During the first 12 h the released species have spherical nanoparticulate form, but after 12 h larger aggregated species were observed to be released. These results indicate that initially the outer surface of the capsule loses a protein layer and then pores are created that the lysozyme fibrils that form the inner sphere of the capsules to dissociate. Finally, dissociation of the entire capsule was observed.

ζ-Potential

The change of ζ-potential values for lysozyme protein capsules was studied as a function of microfluidic channel width change and change to the aqueous:oil flow rates ratio. The results are summarised in FIG. 6 (graph at bottom). ζ-potential, i.e. electric potential, was measured by dynamic light scattering (DLS) based on the detection of changes in electrophoretic mobility of the colloidal particles as a function of mass/volume.

Release Studies

The release study looked at whether the protein molecules forming part of the internal structure of the capsule would be released. Capsules were washed and protein concentration in the washing solution was measured. The highest values of 25% and 40% for the protein molecules which come out due to the washing capsules was reached after 10 min and after 10 hours. After 12 h. the amount of protein that came out of the capsule structure remain low (3%) and stable for the rest of the time (studies were performed for 3 days washing). The surface of the capsule is not smooth which indicates the presence of the protein on the outer surface of the capsule. By following the morphological changes of the capsule against washing time it was found that, in a first step, salt crystals detach from protein capsule surface and then protein attached to the outer surface of the capsule is detached making the surface of the capsule smooth (see FIG. 6).

Following this step, pores form on the surface of the capsule which grow in size with an increase in the capsule washing time. The maximum pore size reached after 12 hours washing with around 300 nm in its size. The morphology of the released species also changes with the increase in washing time. During the first 12 hours the released species have spherical nanoparticulate form. After 12 hours the presence of fibrils was detected. These results indicate that at the first stage the outer surface of the capsule loses its protein layer and then follows the creation of the pores which allows to water molecules to penetrate to the internal part of the capsule and dissolve the lysozyme fibrils which hold the inner part of the capsule. As soon as majority of the fibrils come out of the capsule, the capsule shrinks and loses its spherical form (after 3 days washing). The image of the shrunken capsule is presented in FIG. 6.

The proposed mechanism of the release was confirmed by following the changes in crystallinity of the lysozyme capsules. As prepared capsules (for crystal structure studies capsules were prepared without presence of salt in the precursor mixture) have a definite crystal structure with diffraction parameters identical to lysozyme crystallinity known from the literature (See TEM images and its diffractions in FIG. 12). The lysozyme capsules as well as the precursor mixture and released fraction was analysed. The x-ray diffraction analysis was performed for aqueous lysozyme solution, lysozyme seeds, as prepared lysozyme capsule, capsule after the release, and for fragments which were released from the capsules. All the studies were performed for the samples without presence of NaCl, in order to avoid the misinterpretation of protein crystal structure.

The results are set out in FIG. 12. For a prepared lysozyme capsule, a highly crystalline tetragonal structure was detected. After the capsule was washed and lost its protein layer, the crystallinity of the capsule changed to amorphous. The fibril fragments released from the internal part of the capsules have an amorphous structure (no diffraction was detected). The released nano-particulate protein aggregates were found as a diffractive sample with high tetragonal crystal structure. For the precursor mixture of aqueous seeds the diffraction showed a tetragonal structure. For the lysozyme solution an amorphous structure was detected. From the crystallinity information obtained from x-ray diffraction, it was possible to detect the locations of the seeds as well as lysozyme fibrils. The seeds were located on the membrane as well as in inner part of the capsule. When the capsule was washed for the release studies, the seeds of the lysozyme protein were the first fragment which released from the capsule structure.

Egg Protein Studies

Further capsules were prepared from egg proteins.

Figure 14:
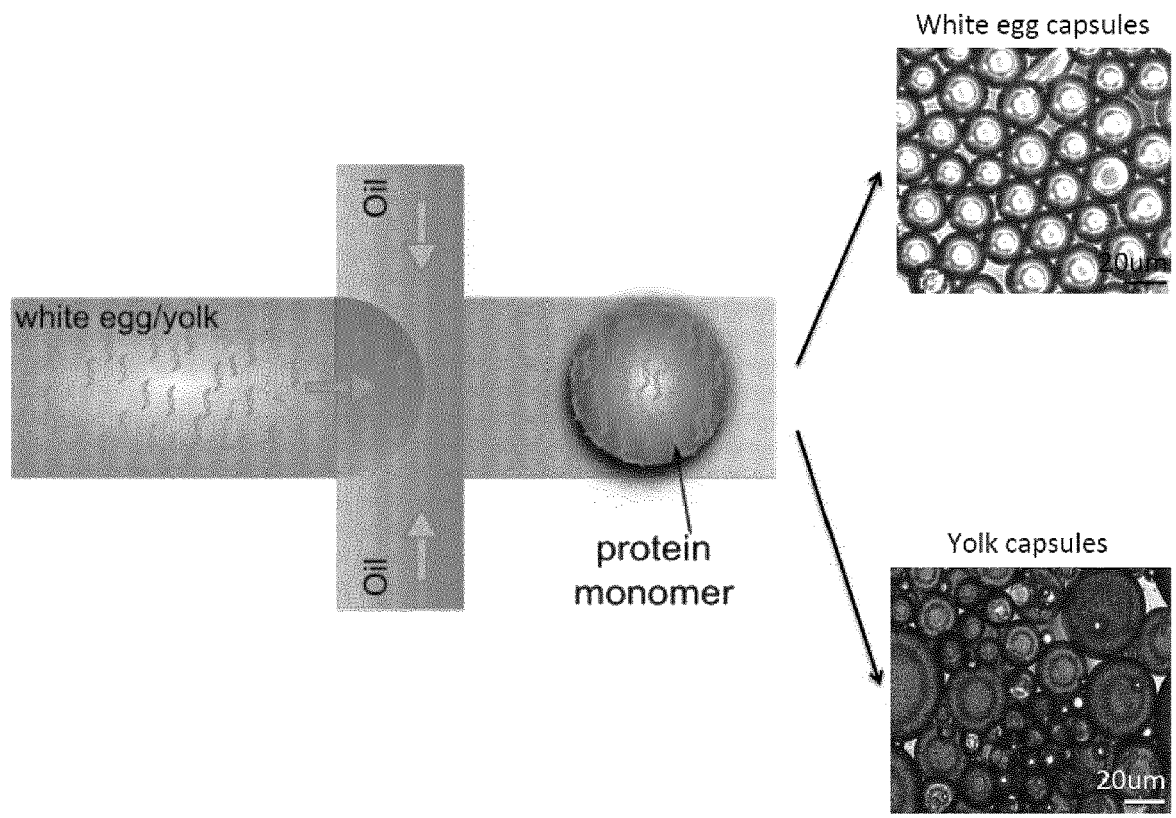
FIG. 14 is a schematic of a method of preparing a capsule according to an embodiment of the invention from the assembly of egg white or egg yolk proteins. The light microscopy images on the right show egg white capsules (top) and egg yolk capsules (bottom). The scale bar is 20 μm.
Figure 15:
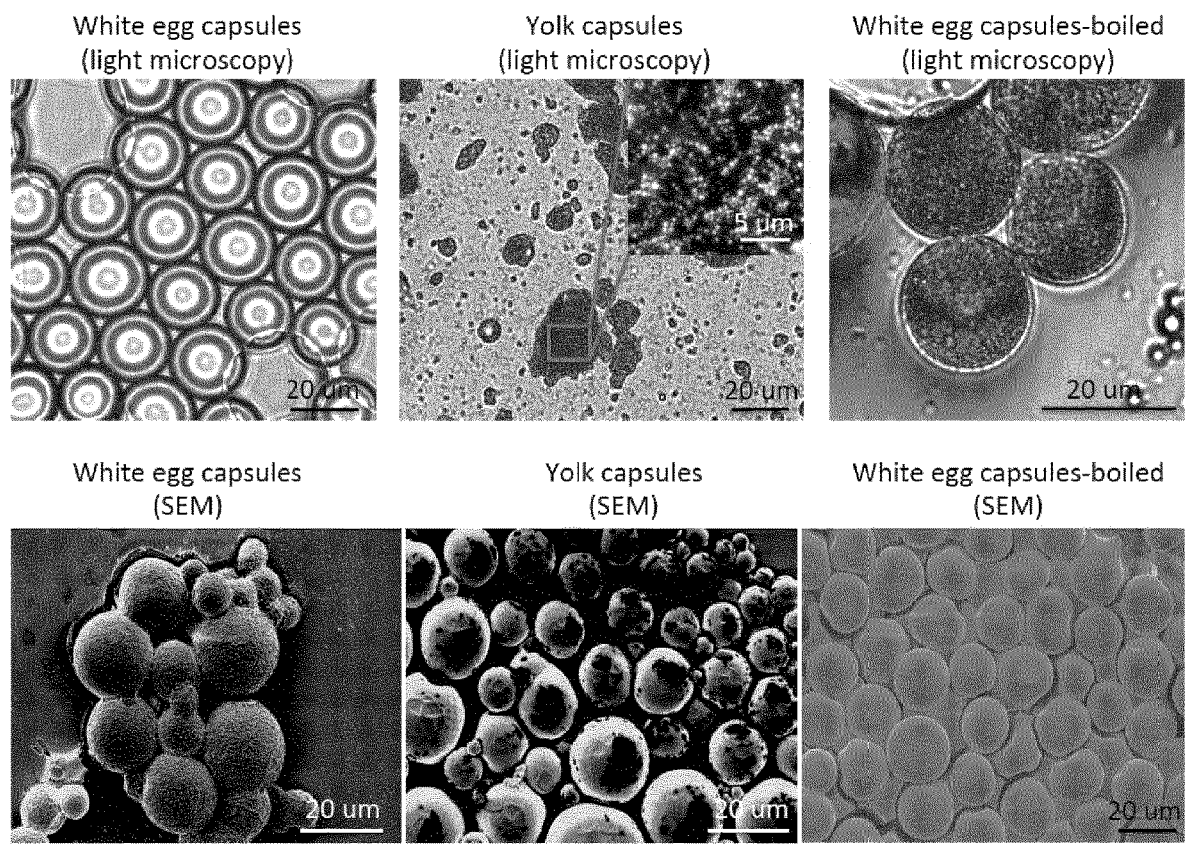
FIG. 15 is a series of light microscope (top) and SEM images (bottom) of egg white capsules (left), egg yolk capsules (centre) and boiled egg white capsules (right). The scale bar is 20 μm for all images.

Capsules were prepared from egg white and egg yolk using the general techniques described above. The microscopy images (bright field and SEM) are shown in FIGS. 14 and 15.

A microfluidic droplet maker was fabricated in polydimethylsiloxane (PDMS) using soft lithography techniques, as described above. Microdroplets were generated by flow-focusing from solutions of raw egg, using one of (i) the ovalbumin rich content of the chicken egg; and (ii) yolk, with a continuous outer phase consisting of FC40 fluorinated oil (Sigma) containing 2% w/v of N,N-bis(n-propyl) polyethylene oxide-bis(2-trifluoromethyl polyperfluoroethylene oxide) amide surfactant.

After the microdroplets were formed, they were incubated for 24 h at 65° C. to promote protein fibrillation. The emulsion phase at the oil-water interface was collected and washed three times.

Solid samples were prepared from egg white droplets. Thus, freshly prepared and collected egg white droplets were boiled at 100° C. for 5 min. The boiled capsules were separated from the residue aqueous solution, which made the later capsule collections easier. The capsules then were dried under air for 2 h.

Multishell Capsules

The capsules of the invention may be prepared as multi-shell (or nested) capsules. These multishell capsules were compared to single-shell capsules such as described above, and additional capsules were prepared using alternative proteins, as detailed below.

Figure 7:
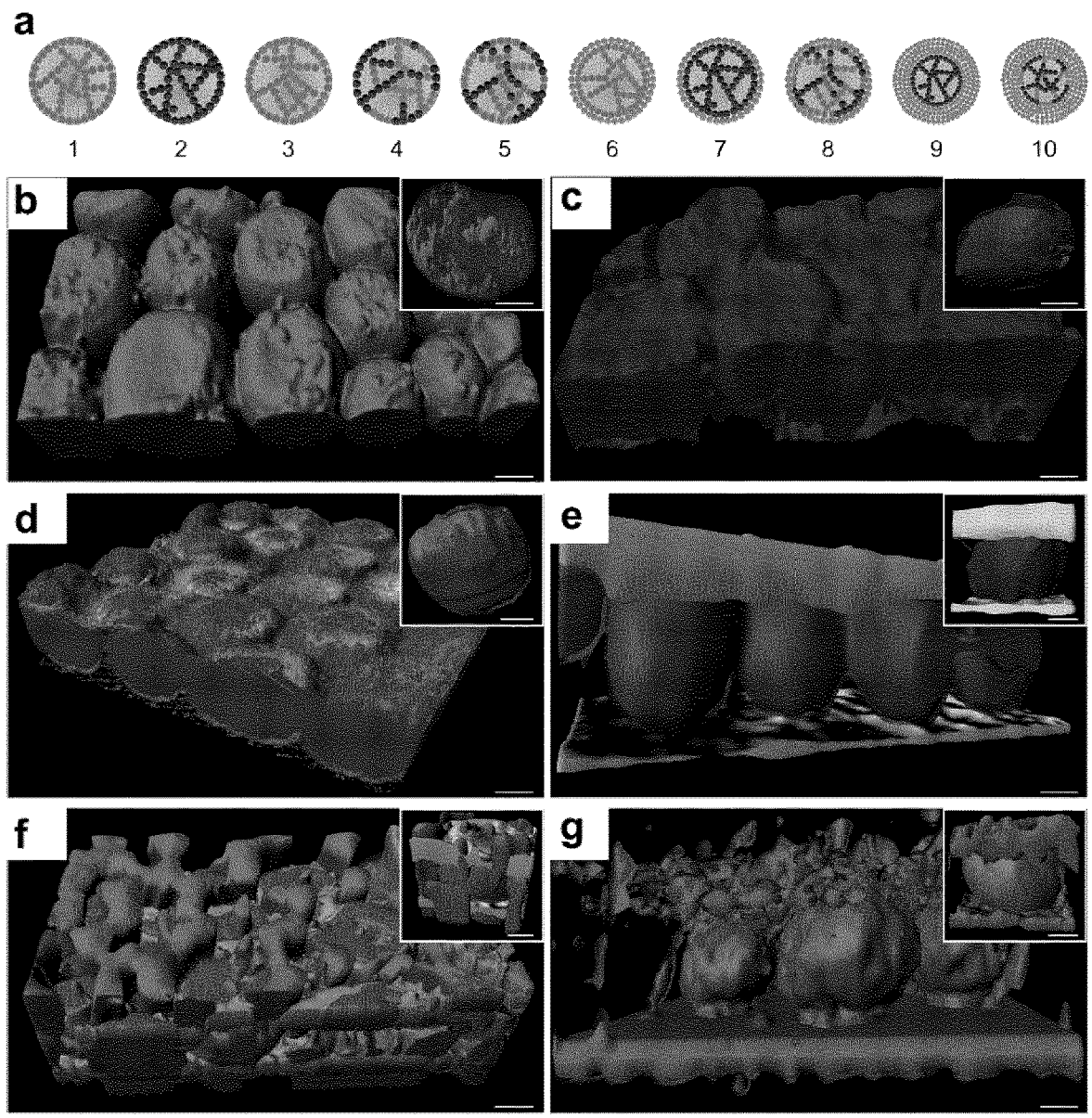
FIG. 7 shows (a) schematic representations of single and multilayered capsule structures formed by microfluidic techniques. Insulin protein marked with red colour, glucagon with blue and lysozyme in green, where 1 is an all-insulin capsule, 2 is an all glucagon capsule and 3 is an insulin and lysozyme capsule, and so on. 3D reconstructions of z-stack confocal images are shown for (b) a single shell insulin capsule; (c) a single shell gel particle made of mixture of glucagon and insulin; (d) a double shell glucagon-lysozyme gel, where glucagon is localised in the core of the gel particle, while lysozyme is localised in the particle shell; (e) a particle where the core of the capsule is formed from glucagon and insulin mixture, which core is wrapped by a lysozyme outer shell; (f) a four shell capsule constructed from (from core to shell) glucagon, lysozyme, insulin and lysozyme; and g) a capsule with glucagon-lysozyme mixture in the core and insulin-lysozyme mixture for the outer shell. Scale Bar=5 µm.
Figure 10:
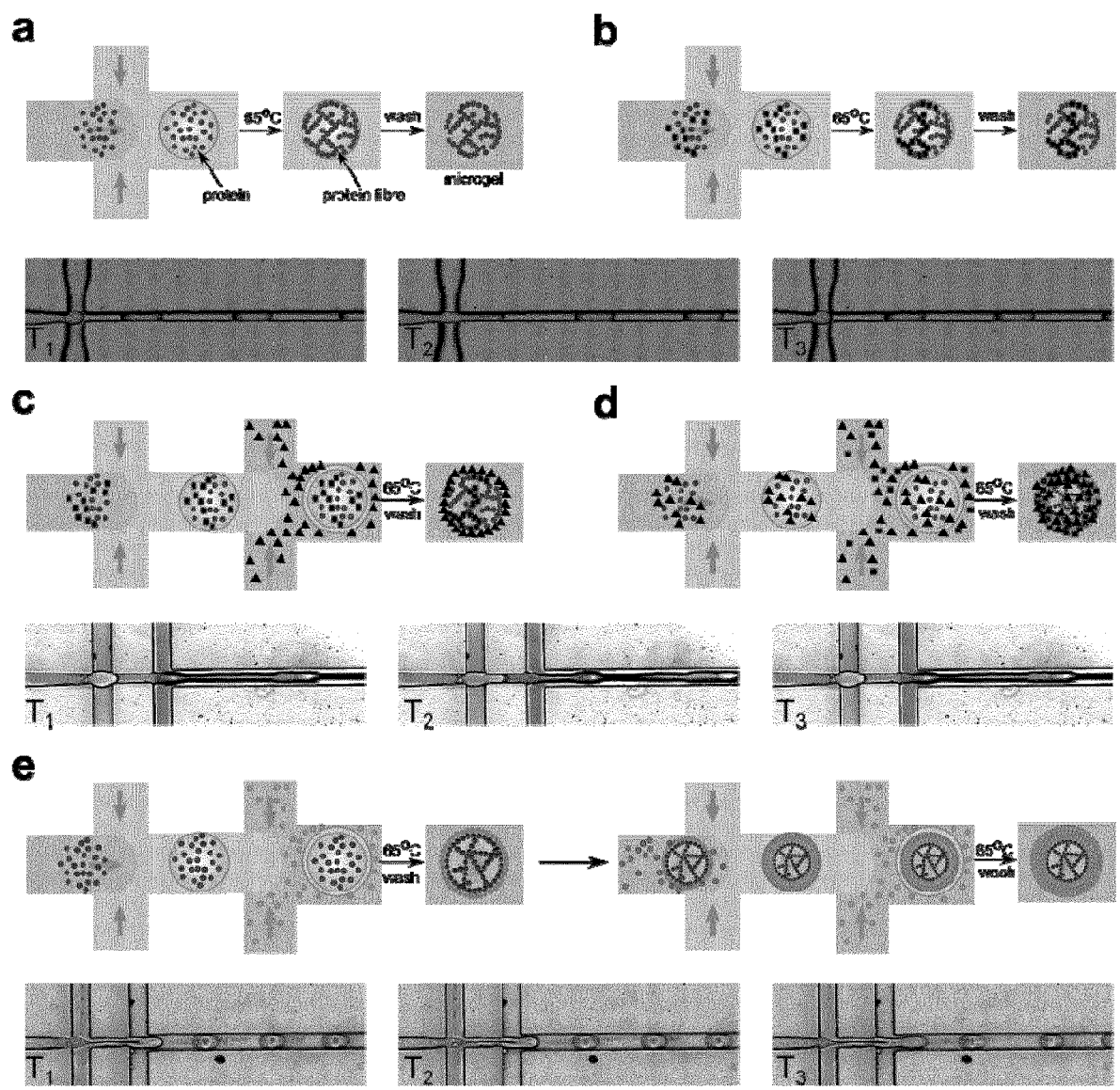
FIG. 10 shows a schematic representation of methods for the formation of such capsules and images of the microfluidic structures for use in the their formation, where (a) shows the formation of a capsule having a shell that is an assembly of a protein, the capsule further comprising a network within the shell that is also an assembly of the protein; (b) shows the formation of a capsule having a shell that is an assembly of a two proteins (represented by squares and circles), the capsule further comprising a network within the shell that is also an assembly of the two proteins; (c) shows the formation of a capsule having a shell that is an assembly of a first protein (represented by a triangle), the further comprising a network within the shell that is an assembly of second and third proteins (represented by squares and circles); (d) shows the formation of a capsule having a shell that is an assembly of first and second proteins (represented by triangles and squares), the capsule further comprising a network within the shell that is also an assembly of first and third proteins (represented by triangles and circles); and (e) shows the formation of a nested capsule having multiple shells of first, second and third proteins, and further comprising an inner shell that is an assembly of a fourth protein, and the inner shell having a network within the shell that is also an assembly of the fourth protein.
Figure 11:
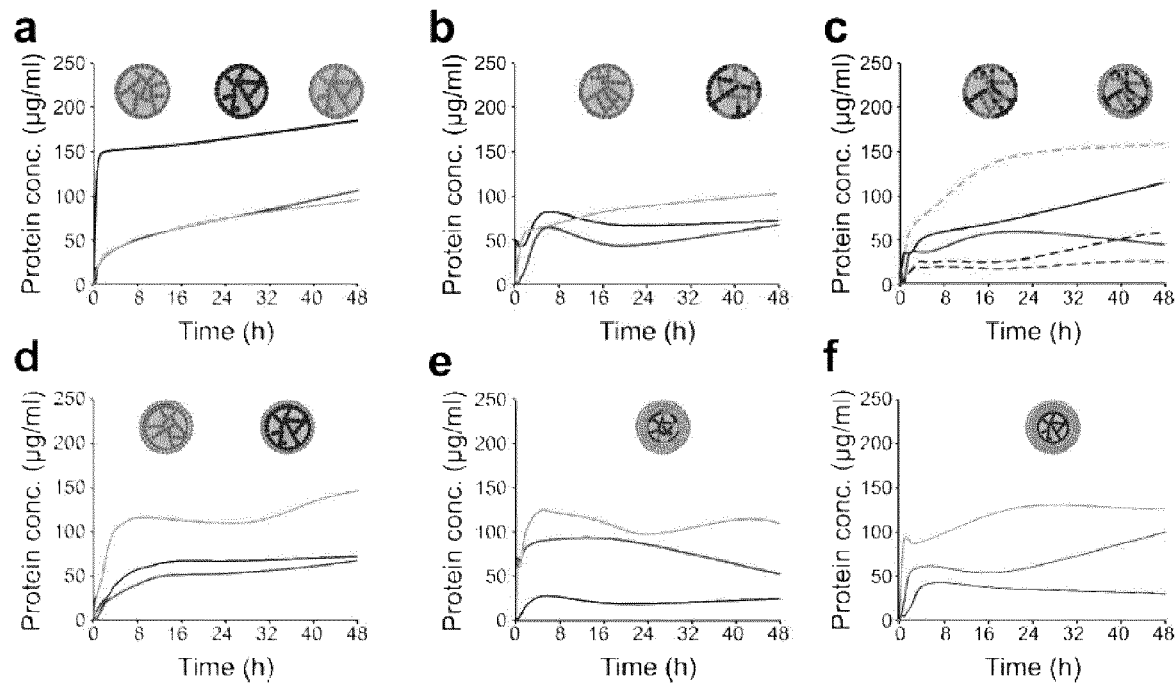
FIG. 11 is a series of six graphs showing the changes in protein concentration (μg/mL) over time (h) for six different capsule structures, where (a) shows the release from lysozyme capsules and structures 1 and 2; (b) shows the release from structures 3 and 4; (c) shows the release from structures 5 and 8 (dashed lines); (d) shows the release from structures 6 and 7; (e) shows the release from structure 10; and (f) shows the release from structure 9. The lysozyme protein release is marked with green line, glucagon with blue and insulin with red, and the capsule numbering refers to that shown in FIG. 7.

Single-shell were synthesised as described above, and multishell capsules were synthesised in a similar manner by forming microdroplets of a protein precursor solution, typically an acidic aqueous protein precursor solution, in an immiscible oil phase in a microfluidic droplet maker device (see below). In these preparations a seed was not used. The schematic representation of the microfluidically formed single and multishell capsule structures is shown in FIG. 7(a) and FIG. 10. The single-shell capsule structures were prepared from one protein or a mixture of two different proteins (see FIG. 1(a)). Single-shell capsules 1-5 in FIG. 1 (a) and FIG. 10 were created in a single T-junction droplet maker (as shown in FIGS. 10 (a) and (b)), while multilayered structures, structures 6-10 in FIG. 1(a) and FIG. 10, were prepared in a double T-junction droplet maker device (see also FIGS. 10 (c) to (e)). Methods for the preparation of nested droplets are also well known in the art.

The amylogenic gelation of the soluble proteins was initiated through droplets emulsion incubation at 65° C. for 12 h (as shown also in FIG. 10). To confirm the structural complicity of the capsules and to allocate the position of each protein in the microgel structure, the capsules were analysed with confocal microscopy, followed by the complete reconstruction of the three-dimensional microgel structure. Each protein component was labelled with a dye specific to that dye: insulin was labelled with CF594 dye (exit. 593 nm/emiss. 614 nm), glucagon with CF350 dye (excit. 347 nm/emus. 448 nm) and lysozyme was labelled with CF488A dye (excit. 490 nm/emiss. 515 nm) (see Dye Staining below). Confocal microscopy analysis results (analysis discussed below), presented in FIG. 7 (b) to (g) show the exact localisation of each protein. A striking difference in the spatial localisation of the fluorescence signal was observed between the capsules produced from a single protein, and a mixture of proteins in a single T-junction device and a double T-junction device. A representative example of each type of capsule is shown illustrated in FIG. 7 (b) to (g).

For capsules formed from one protein in a single T-junction droplet maker, a fluorescent signal was detectable from the entire interior of the particles (FIGS. 1 (b) and (c)) and for other capsules see (FIG. 1 (d) to (g)), a distinguishable difference for fluorescent outer shell/shells was observed. This observation, which correlates with oil fraction studies (FIG. 8 (a)), suggests that the protein localises on the interface between the aqueous and oil phases when the droplets are formed.

The oil fraction trapped between the protein layers linearly increases with the number of protein shells (See FIG. 8 (a)). The efficiency of microfluidic synthesis approach to generate complex multilayered microgel capsule structures was studied as a function of number of shells in the structure. The resultant structures were formed with high efficiency values varied from 87%, for single shell structures, to 78% for more complex multilayered structures as shown in FIG. 8 (b). By contrast, the final size of the structures is restricted only by the mean of the droplet maker channel width (25 µm).

Materials Summary

The following materials were used for microgel protein shells preparation: human glucagon (Gemini Bio-Products) and insulin proteins (Sigma-Aldrich), lysozyme human protein (Sigma-Aldrich), fluorinert FC70 (Sigma) and N,N-bis-(n-propyl) polyethylene oxide-bis(2-trifluoromethyl polyperfluoroethylene oxide) amide surfactant. For release mechanism and kinetics studies: Thioflavin T (Tht) (Sigma-Aldrich) dye was used.

Dye Staining Assay

The staining was performed on precursor proteins using "mix and stain" CF594 (exit. 593 nm/emiss. 614 nm), CF350 (excit. 347 nm/emus. 448 nm) and CF488A (excit. 490 nm/emiss. 515 nm) dyes (Sigma-Aldrich). The proteins were first transferred to reaction buffer (supplied by Sigma-Aldrich) and then mixed with the dyes. The insulin was labelled with CF594 dye, glucagon with CF350 dye and lysozyme was labelled with CF488A dye.

Confocal Microscopy

For confocal fluorescent microscopy, samples were prepared by depositing the aqueous dispersions, without further purification, onto a glass slide. The protein microgels were analysed by confocal microscopy (Laser Scan Confocal, Zeiss Microscope) using following lasers: UV 405 nm at 25 mW (for violet excitations) and tenable Argon 458/477/488/514 nm at 30 mW (for green excitations detection) and Ne 594 nm at 30 mW (for red excitation). 3D images were reconstructed using the confocal z-stacked images (in average 500 z-stack slices per each protein shell).

Atomic Force Microscopy

Protein microgels were analysed and characterised by AFM microscope, H-02-0067 NanoWizard II (JPK Instruments) by depositing protein fibrils on mika surface. In order to extract protein fibrils from microgel structures, the microgels were centrifuged for 1 h at room temperature at 13,000 rpm.

Efficiency, Loading Capacity and Release Kinetics Measurements

The efficiency of microfluidic techniques for protein capsules synthesis was studied by calculating the percentage of protein participating in capsule formation following the fluorescent signal of labelled protein in residue solutions. After the preparation of the microgel capsules was accomplished and the resulting capsules were washed, in order to remove unreacted species, and the concentration of unreacted protein was calculated following UV absorption and fluorescent signal of each protein. In order to study the release kinetics of insulin, glucagon and lysozyme protein microgel shells, the loaded samples were washed with DDW pH=7 within following intervals of time: 10 min., 30 min., 1 h., 3 h., 8 h., 12 h., 24 h., 48 h., 3 d., 7 d. Each washing solution was than analysed by UV spectroscopy and fluorimeter and exact concentration of the released species was detected.

In order to understand and predict the protein release rates, the mechanism of microdroplets gelation was studied by following the protein fibrillation (aggregation) kinetics in single shell gel droplets (for single shell insulin, glucagon and lysozyme microgels) and this was compared with to aggregation kinetics of free proteins. The fraction of fibrillated protein material was detected by following the enhanced and red-shifted fluorescence of Thioflavin-T (ThT) dye upon binding to amyloid fibrils over time. FIG. 8 (c) shows the aggregation kinetics study results for insulin, glucagon and lysozyme proteins in their free and capsule forms. Slower aggregation rates were observed for proteins in capsule form compared to the free protein form. This observation is explained by the physical limitation of the amyloid protein fibril growth in the droplets. The insulin, glucagon and lysozyme protein fibrils that were grown within droplets were found to be shorter (by around five orders of magnitude) compering to free protein fibrils, as shown in AFM images FIG. 8 (d). Moreover, the protein nanofibres tend to grow as dense agglomerates (see FIG. 8 (d) capsule fibres) rather than long fibres (see FIG. 2 (d) fibres).

Finally, whether the aggregation nature of the protein structures influenced the release kinetics of the encapsulated proteins was studied. The data in FIGS. 9 (a) and (c) shows a marked difference in the release of insulin, glucagon and lysozyme proteins. Interestingly, the release rates for the glucagon protein are much faster compared to insulin and lysozyme proteins. This effect is attributed to the slow aggregation process of glucagon protein in the protein assembly. However, for the multishell structures, the proteins which localise at the core of the microgels tend to dissociate (release) only after the proteins of the outer shell are released. The representative examples for the mechanism of the single shell and multishell microgels dissociation and protein release are shown in FIG. 9, respectively.

ThT Assay

The incorporation of glucagon, insulin and lysozyme proteins monomers into the amyloid fibrils' structure inside the microgels was studied following the changes in fluorescent intensities of Thioflavin T dye molecules emission at 490 nm. The $6:58\times10^{-5}$ M ThT dye was added to the microfluidically formed protein droplets. The proteins amyloid fibrillation, droplets gelation and incorporation of the ThT dye into gels' structures was achieved by incubation of the gels with dye for 10 min., 30 min., 1 h., 3 h., 8 h., 12 h. and 24 h at 65° C. After gelation was accomplished, the microgels were washed with acidic (pH=2) DDW in order to remove the surfactant, unreacted protein residues and excess of ThT dye. The fluorescent intensity profile of single lysozyme capsule gel was measured by fluorescent microscopy using ThT filter (excit. 440 nm/emiss. 490 nm).

REFERENCES

A number of publications are cited above in order to more fully describe and disclose the invention and the state of the art to which the invention pertains. Full citations for these references are provided below. The entirety of each of these references is incorporated herein.

Anna et al. *Applied Physics Letters* 2003, 82, 364
Bartus et al. *Science* 281, 1161-1162 (1998)
Booth et al. *Nature* 385, 787 (1997)
Cole et al. *Cancer Chemother. Pharmacol.* 1986, 17, 259
Diez-Pascual et al. *J. Colloid Interface Sci.* 347, 79-89 (2010)
Dobson *Nature* 426, 884-890 (2003)
Feng et al. *Bioresour. Technol.* 128, 107-112 (2013)
Fowler et al. *European Journal of Oral Sciences* 114, 297-303 (2006)
Holtze et al. *Lab Chip* 2008, 8, 1632
Hsu et al. *J. Phys. Chem. B* 2013, 4, 3459
Jia, X. et al. *Biomacromolecules* 7, 3336-3344 (2006)
Knowles et al. *Nat. Nanotechnol.* 6, 469-479 (2011)
Langer et al. *Nature* 428, 487-492 (2004)
Li et al. *Advanced Materials* 25, 3694-3700 (2013)
Li et al. *Nat. Nano* 7, 421-427 (2012)
Maji, S. K. et al. *PLoS Biol.* 6, e17 (2008)
O'Brien et al. *Canadian Journal of Chemistry* 59, 1878-1887 (1981)
Paparcone et al. *Biochemistry* 49, 8967-8977 (2010)
Peer et al. *Nat. Nano.* 2, 751-760 (2007)
Qin et al. *Nature Protocols* 2010, 5, 491
Sagis et al. *Langmuir* 2008, 24, 1608
Seiffert et al. *Langmuir* 26, 14842-14847 (2010)
Shimanovich et al. *Advanced Functional Materials* 21, 3659-3666 (2011)
Sipe et al. *Amyloid* 2010, 17, 101
Suh et al. *J. Am. Chem. Soc.* 134, 7337-7343 (2012)
US 2011/0280944
US 2013/0136779

US 2014/0023688 Uversky et al. *Biochimica et Biophysica Acta* 2004, 1698, 131
Wang et al. *Lab Chip* 13, 2547 (2013)
Wei-Chun Chin et al. *Nature* 391, 568-572 (1998)
WO 2013/120856
Yang et al. *Lab Chip* 2009, 9, 961
Zhang et al. *Nat. Biotech.* 21, 1171-1178 (2003)

The invention claimed is:

1. A population of capsules, wherein each capsule comprises a shell of material that comprises of a self-assembly of one or more proteins, wherein the self-assembly of the one or more proteins is an amyloid assembly of the one or more proteins held together by non-covalent interactions between neighboring protein molecules, wherein the population of capsules is formed by a method comprising:
 (i) contacting a flow of a first phase and a flow of a second phase in a channel, thereby generating in the channel a dispersion of discrete regions of the second phase in the first phase, wherein one of the first or second phase is an aqueous phase and the other phase is a water immiscible phase, and the one of the first and second phase comprises one or more proteins suitable for self-assembly, wherein the one or more proteins is provided in monomeric form and is soluble;
 (ii) permitting the one or more proteins to self-assemble at the boundary layer of the discrete regions between the first and second phases under denaturing conditions; and
 (iii) optionally collecting the outflow from the channel, thereby obtaining a droplet, which contains a capsule, and wherein the one or more proteins each comprise 50 or more amino acids,
 and wherein the droplets have a size distribution having a relative standard deviation (RSD) of at most 10%, and wherein each capsule has an average diameter in the range of 0.5 μm to 100 μm.

2. The population of capsules of claim 1, wherein the self-assembly of the one or more proteins is a fibril assembly.

3. The population of capsules of claim 1, wherein each capsule further comprises a network within the shell that is a self-assembly of one or more proteins, wherein the network is optionally connected to the shell.

4. The population of capsules of claim 3, wherein the network is an amyloid assembly of the one or more proteins.

5. The population of capsules of claim 1, wherein the one or more proteins is selected from the group consisting of glucagon, myoglobin, haemoglobin, bovine serum albumin (BSA), ovalbumin, silk, egg yolk, immunoglobulin light chain, immunoglobulin heavy chain, β2-microglobulin, transthyretin, serum AA, apolipoprotein, gelsolin, lysozyme, fibrinogen α-chain, cystatin C, ABriPP, leukocyte chemotactic factor 2, ADanPP, Aβ and Aβ protein precursor (AβPP), prion protein, calcitonin, islet amyloid polypeptide, atrial natriuretic factor, prolactin, insulin, lactadherin, kerato-epithelin, lactoferrin, odontogenic ameloblast-associated protein, semenogelin I, α-S2C and K casein, α-synuclein, polyQ expanded huntingtin, actin, neuroserpin, ferritin, tau, androgen receptor protein, ataxin-1, DRPLA, NAC, atrial natriuretic factor, betabellins 15D and 16D, cytochrome $C_{552}$, methionine aminopeptidase, phosphoglycerate kinase, PI3-SH3, β-lactobgolbulin, monellin, HypF, Human complement receptor, human stefin B, GAG factor, yeast prion Ure2p, herpes simplex virus glycoprotein B, adenovirus fibre, α-lactalbumin, β-lactoglobulin, and yeast protein Sup35.

6. The population of capsules of claim 1, wherein a self-assembly of the one or more proteins is substantially free of the oligomer form of that protein or proteins.

7. The population of capsules of claim 1, wherein the shell is a material that is a self-assembly of a plurality of proteins.

8. The population of capsules of claim 1, wherein at least one capsule in the population of capsules is a first capsule holding a second capsule, and each of the first and second capsules consist of a shell of material that is a self-assembly of one or more proteins.

9. The population of capsules of claim 1, wherein at least one capsule in the population of capsules holds a component.

10. The population of capsules of claim 7, further comprising a network within the shell that is a self-assembly of a plurality of proteins, and the shell is a material that is a self-assembly of a plurality of proteins.

11. The population of capsules of claim 1, wherein the capsule shell has pores, and the pore size is:
 (i) at most 0.5 μm; and/or
 (ii) at least 0.5 nm.

12. The population of capsules of claim 1, wherein the water immiscible phase is an oil phase.

13. The population of capsules of claim 1, wherein the one or more proteins each comprises 100 or more amino acids.

14. The population of capsules of claim 1, wherein the capsules are a microgel.

15. A method of preparing the population of capsules of claim 1, the method comprising the steps of:
 (i) contacting a flow of a first phase and a flow of a second phase in a channel, thereby generating in the channel a dispersion of discrete regions of the second phase in the first phase, wherein one of the first or second phase is an aqueous phase and the other phase is a water immiscible phase, and the one of the first and second phase comprises one or more proteins suitable for self-assembly, wherein the one or more proteins is provided in monomeric form and is soluble;
 (ii) permitting the one or more proteins to self-assemble at the boundary layer of the discrete regions between the first and second phases under denaturing conditions; and
 (iii) optionally collecting the outflow from the channel, thereby obtaining a droplet, which contains a capsule.

16. The method of claim 15, wherein the flow rate of the first phase is greater than the flow rate of the second phase.

17. The method of claim 15, wherein the one or more proteins is provided in an aqueous phase.

18. The method of claim 15, wherein the concentration of the one or more proteins in the first phase or second phase is from 0.1 to 200 μM.

19. The method of claim 15, wherein the one or more proteins is provided together with a seed, wherein the seed is an assembly of a plurality of protein molecules.

20. The method of claim 19, wherein:
 (i) the length of the seed is from 10 to 500 nm; and/or
 (ii) the seed is provided in a phase with the protein at 5 mole % or less with respect to the concentration of the protein in the phase; and/or
 (iii) the seed is provided in a phase with the one or more proteins at from 0.02 to 0.5 μM.

21. The method of claim 15, wherein the one or more proteins is selected from the group consisting of glucagon, myoglobin, haemoglobin, bovine serum albumin (BSA), ovalbumin, silk, egg yolk, immunoglobulin light chain, immunoglobulin heavy chain, β2-microglobulin, transthyretin, serum AA, apolipoprotein, such as apolipoprotein AI, AII and AIV, gelsolin, lysozyme, fibrinogen α-chain, cystatin C, ABriPP, leukocyte chemotactic factor 2, ADanPP, Aβ and Aβ protein precursor (AβPP), prion protein, calcitonin, islet amyloid polypeptide, atrial natriuretic factor, prolactin, insulin, lactadherin, kerato-epithelin, lactoferrin, odontogenic ameloblast-associated protein, semenogelin I, α-S2C and K casein, α-synuclein, polyQ expanded huntingtin, actin, neuroserpin, ferritin, tau, androgen receptor protein, ataxin-1, DRPLA, NAC, atrial natriuretic factor, betabellins 15D and 16D, cytochrome $C_{552}$, methionine aminopeptidase, phosphoglycerate kinase, lysozyme, PI3-SH3, β-lactobgolbulin, monellin, HypF, Human complement receptor, human stefin B, GAG factor, yeast prion Ure2p, herpes simplex virus glycoprotein B, adenovirus fibre, α-lactalbumin, β-lactoglobulin, and yeast protein Sup35, such as a protein selected from the group consisting of lysozyme, glucagon, insulin, myoglobin, haemoglobin, bovine serum albumin (BSA), ovalbumin, and silk.

22. The method of claim 15, wherein the second phase further comprises a component for encapsulation, thereby providing a capsule holding the component.

23. A method of delivering the population of capsules of claim 1 to a location, the method comprising the steps of:
  (i) providing the population of capsules of claim 1,
  (ii) delivering the population of capsules to a target location;
  (iii) disrupting the shell material, thereby releasing the one or more proteins and the component.

* * * * *